(12) United States Patent
Geuijen et al.

(10) Patent No.: US 8,551,488 B2
(45) Date of Patent: Oct. 8, 2013

(54) BINDING MOLECULES FOR TREATMENT AND DETECTION OF CANCER

(75) Inventors: Cecilia Anna Wilhelmina Geuijen, Moerkapelle (NL); Cornelis Adriaan De Kruif, El de Bilt (NL)

(73) Assignee: Crucell Holland B.V., Leiden (NL)

(*) Notice: Subject to any disclaimer, the term of this patent is extended or adjusted under 35 U.S.C. 154(b) by 468 days.

(21) Appl. No.: 12/803,125

(22) Filed: Jun. 18, 2010

(65) Prior Publication Data

US 2010/0297153 A1 Nov. 25, 2010

Related U.S. Application Data

(63) Continuation of application No. 11/665,102, filed as application No. PCT/EP2005/055163 on Oct. 11, 2005, now Pat. No. 7,858,086.

(60) Provisional application No. 60/618,332, filed on Oct. 12, 2004.

(30) Foreign Application Priority Data

Oct. 12, 2004 (EP) .................................. 04104999

(51) Int. Cl.
*A61K 39/395* (2006.01)
*A61K 38/16* (2006.01)
*C07K 16/30* (2006.01)

(52) U.S. Cl.
USPC ................. 424/174.1; 514/19.3; 530/387.9; 530/398.7

(58) Field of Classification Search
USPC .......... 424/174.1; 514/19.3; 530/387.9, 398.7
See application file for complete search history.

(56) References Cited

U.S. PATENT DOCUMENTS

| | | | |
|---|---|---|---|
| 7,329,530 B2 | 2/2008 | Houtzager et al. | |
| 7,579,446 B2 | 8/2009 | Bakker et al. | |
| 7,740,852 B2 | 6/2010 | Bakker et al. | |
| 7,858,086 B2* | 12/2010 | Geuijen et al. | 424/133.1 |
| 2006/0121580 A1 | 6/2006 | ter Meulen et al. | |
| 2007/0042359 A1 | 2/2007 | Throsby et al. | |
| 2007/0122801 A1 | 5/2007 | Throsby et al. | |
| 2008/0014204 A1 | 1/2008 | ter Meulen et al. | |
| 2008/0070799 A1 | 3/2008 | Bakker et al. | |
| 2008/0095780 A1 | 4/2008 | Geuijen et al. | |
| 2009/0017521 A1 | 1/2009 | Houtzager et al. | |
| 2009/0054254 A1 | 2/2009 | Throsby et al. | |
| 2009/0104204 A1 | 4/2009 | Throsby et al. | |
| 2009/0130652 A1 | 5/2009 | Throsby et al. | |
| 2009/0169562 A1 | 7/2009 | Throsby et al. | |
| 2009/0311265 A1 | 12/2009 | van den Brink et al. | |
| 2010/0146647 A1 | 6/2010 | Logtenberg et al. | |

FOREIGN PATENT DOCUMENTS

| | | |
|---|---|---|
| WO | WO 00/61180 | 10/2000 |
| WO | WO 03/063796 | 8/2003 |
| WO | WO 03/087768 | 10/2003 |
| WO | WO 2004/043344 | 5/2004 |
| WO | WO 2004/003019 | * 6/2004 |

OTHER PUBLICATIONS

Lederman et al (Molecular Immunology 28:1171-1181, 1991).*
Li et al (Proc. Natl. Acad. Sci. USA 77:3211-3214, 1980).*
Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. ((1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Boel E., S. Verlaan, M.J. Poppelier, N.A. Westerdaal, J.A. Van Strijp, and T. Logtenberg (2000). Functional human monoclonal antibodies of all isotypes constructed from phage display library-derived single-chain Fv antibody fragments. *J. Immunol. Methods* 239:153-166.
Burton D.R. and C.F. Barbas (1994), Human antibodies from combinatorial libraries. *Adv. Immunol.* 57:191-280.
De Kruif J., L. Terstappen, E. Boel, and T. Logtenberg (1995a). Rapid selection of cell subpopulation-specific human monoclonal antibodies from a synthetic phage antibody library. *Proc. Natl. Acad. Sci. USA* 92:3938.
De Kruif J., E. Boel and T. Logtenberg (1995b). Selection and application of human single chain Fv antibody fragments from a semi-synthetic phage antibody display library with designed CDR3 regions. *J. Mol. Biol.* 248:97.
Huls G., I.J. Heijnen, E. Cuomo, J. van der Linden, E. Boel, J. van de Winkel and T. Logtenberg (1999). Antitumor immune effector mechanisms recruited by phage display-derived fully human IgG1 and IgA1 monoclonal antibodies. *Cancer Res.* 59:5778-5784.
Pappin D.J.C., P. Hojrup and A. Bleasby (1993). Rapid identification of proteins by peptide-mass fingerprinting. *Curr. Biol.* 3:327-332.
Streuli M., N.X. Krueger, L.R. Hall, S.F. Schlossman, and H. Saito (1988). A new member of the immunoglobulin superfamily that has a cytoplasmic region homologous to the leukocyte common antigen. *J. Exp. Med.* 168:1523-1530.

(Continued)

*Primary Examiner* — Lynn Bristol
(74) *Attorney, Agent, or Firm* — TraskBritt

(57) ABSTRACT

Provided are new tumor-associated antigens, binding molecules that specifically bind to the antigens, nucleic acid molecules encoding the binding molecules, compositions comprising the binding molecules, and methods of identifying or producing the binding molecules. The tumor-associated antigens are expressed on cancer cells and binding molecules capable of specifically binding to the antigens can be used in the diagnosis, prevention and/or treatment of cancer.

12 Claims, 9 Drawing Sheets

(56) References Cited

OTHER PUBLICATIONS

Streuli M., N.X. Krueger, P.D. Ariniello, M. Tang, J.M. Munro, W.A. Blattler, D.A. Adler, C.M. Disteche, and H. Saito (1992). Expression of the receptor-linked protein tyrosine phosphatase LAR: proteolytic cleavage and shedding of the CAM-like extracellular region. *EMBO J.* 11:897-907.

Brandt et al. "Aberrant Expression of CD19 as a Maker of Monocytic Lineage in Acute Myelogenous Leukemia" vol. 107, No. 3 pp. 283-291 (10 pages), (Mar. 1997).

Gueijen et al. "A Proteomic Approach to Tumour Target Idenification Using Phage Display, Affinity Purification and Mass Spectrometry" European Journal of Cancer 41 (2005) pp. 178-187 (10 pages).

Myers et al. "Large Scale Manufacturing of TXU(Anti-CD7)-Pokeweed Antiviral Protein (PAP) Immunoconjugate for Clinical Trials" Overseas Publisher Association Amersterdam B.V. (1997) Published in The Netherlands by Harwood Academic Publishers pp. 257-285 (28 pages).

Streuli et al. "Expression of the Receptor-Linked Protein Tyrosine Phsphatase LAR: Proteolytic Cleavage and Shedding of the CAM-Like Extracellular Region" The EMBO Journal (1992) vol. 11 No. 3 pp. 897-907 (12 pages).

International Preliminary Report on Patentability for PCT/EP/2005/055163 on Jul. 12, 2006 (12 pages).

U.S. Appl. No. 11/919,265, filed Oct. 24, 2007, Throsby et al., Host Cell Specific Binding Molecules Capable of Neutralizing Viruses and Uses Thereof.

U.S. Appl. No. 12/590,973, filed Nov. 16, 2009, ter Meulen et al., Binding Molecules Against SARS-Coronavirus and Uses Thereof.

U.S. Appl. No. 12/459,661, filed Jul. 6, 2009, Bakker et al., Binding Molecules Capable of Neutralizing Rabies Virus and Uses Thereof.

U.S. Appl. No. 12/310,812, filed Mar. 6, 2009, van den Brink et al., Human Binding Molecules Capable of Neutralizing Influenza Virus H5N1 and Uses Thereof.

U.S. Appl. No. 12/798,748, filed Apr. 8, 2010, Bakker et al., Binding Molecules Capable of Neutralizing Rabies Virus and Uses Thereof.

* cited by examiner

SEQUENCE LISTING

<160> NUMBER OF SEQ ID NOS: 67

<210> SEQ ID NO 1
<211> LENGTH: 12
<212> TYPE: PRT
<213> ORGANISM: Artificial sequence
<220> FEATURE:
<223> OTHER INFORMATION: HCDR3 SC02-401

<400> SEQUENCE: 1

Asp Asp Thr Pro Thr Ser Asp Tyr Gly Phe Asp Ser
1               5                   10

<210> SEQ ID NO 2
<211> LENGTH: 9
<212> TYPE: PRT
<213> ORGANISM: Artificial sequence
<220> FEATURE:
<223> OTHER INFORMATION: HCDR3 SC02-361

<400> SEQUENCE: 2

Trp Ala Pro Ser His Ser Phe Asp Tyr
1               5

<210> SEQ ID NO 3
<211> LENGTH: 121
<212> TYPE: PRT
<213> ORGANISM: Artificial sequence

```
<220> FEATURE:
<223> OTHER INFORMATION: Variable heavy chain SC02-401

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Thr Pro Thr Ser Asp Tyr Gly Phe Asp Ser Trp Gly
            100                 105                 110

Gln Gly Thr Leu Val Thr Val Ser Ser
        115                 120

<210> SEQ ID NO 4
<211> LENGTH: 118
<212> TYPE: PRT
<213> ORGANISM: Artificial sequence
<220> FEATURE:
<223> OTHER INFORMATION: Variable heavy chain SC02-361

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Trp Ala Pro Ser His Ser Phe Asp Tyr Trp Gly Gln Gly Thr
            100                 105                 110

Leu Val Thr Val Ser Ser
        115

<210> SEQ ID NO 5
<211> LENGTH: 1761
<212> TYPE: DNA
<213> ORGANISM: Homo sapiens
<220> FEATURE:
<221> NAME/KEY: CDS
<222> LOCATION: (1)..(1761)
<223> OTHER INFORMATION: Nucleotide sequence encoding AML-associated
      antigen

<400> SEQUENCE: 5 atg tcg tgg ctc ttc ggc att aac aag ggc ccc aag ggt gaa gac gcg    48
Met Ser Trp Leu Phe Gly Ile Asn Lys Gly Pro Lys Gly Glu Asp Ala
1               5                   10                  15
```

| | | |
|---|---|---|
| ggg ccg ccg ccg cct ttg ccg ccc gcg cag ccc ggg gcc gag ggc ggc<br>Gly Pro Pro Pro Pro Leu Pro Pro Ala Gln Pro Gly Ala Glu Gly Gly<br>        20                       25                   30 | | 96 |
| ggg gac cgc ggc ttg gga gac cgg ccg gcg ccc aag gac aaa tgg agc<br>Gly Asp Arg Gly Leu Gly Asp Arg Pro Ala Pro Lys Asp Lys Trp Ser<br>           35                     40                   45 | | 144 |
| aac ttc gac ccc acc ggc ctg gag cgc gcc gcc aag gcg gcg cgc gag<br>Asn Phe Asp Pro Thr Gly Leu Glu Arg Ala Ala Lys Ala Ala Arg Glu<br>50                        55                     60 | | 192 |
| ctg gag cac tcg cgt tat gcc aag gac gcc ctg aat ctg gca cag atg<br>Leu Glu His Ser Arg Tyr Ala Lys Asp Ala Leu Asn Leu Ala Gln Met<br>65                     70                    75                  80 | | 240 |
| cag gag cag acg ctg cag ttg gag caa cag tcc aag ctc aaa gag tat<br>Gln Glu Gln Thr Leu Gln Leu Glu Gln Gln Ser Lys Leu Lys Glu Tyr<br>                 85                     90                   95 | | 288 |
| gag gcc gcc gtg gag cag ctc aag agc gag cag atc cgg gcg cag gct<br>Glu Ala Ala Val Glu Gln Leu Lys Ser Glu Gln Ile Arg Ala Gln Ala<br>                     100                  105                110 | | 336 |
| gag gag agg agg aag acc ctg agc gag gag acc cgg cag cac cag gcc<br>Glu Glu Arg Arg Lys Thr Leu Ser Glu Glu Thr Arg Gln His Gln Ala<br>                 115                  120                125 | | 384 |
| agg gcc cag tat caa gac aag ctg gcc cgg cag cgc tac gag gac caa<br>Arg Ala Gln Tyr Gln Asp Lys Leu Ala Arg Gln Arg Tyr Glu Asp Gln<br>        130                  135                140 | | 432 |
| ctg aag cag cag caa ctt ctc aat gag gag aat tta cgg aag cag gag<br>Leu Lys Gln Gln Gln Leu Leu Asn Glu Glu Asn Leu Arg Lys Gln Glu<br>145                     150                  155                160 | | 480 |
| gag tcc gtg cag aag cag gaa gcc atg cgg cga gcc acc gtg gag cgg<br>Glu Ser Val Gln Lys Gln Glu Ala Met Arg Arg Ala Thr Val Glu Arg<br>                 165                  170                175 | | 528 |
| gag atg gag ctg cgg cac aag aat gag atg ctg cga gtg gag gcc gag<br>Glu Met Glu Leu Arg His Lys Asn Glu Met Leu Arg Val Glu Ala Glu<br>        180                  185                190 | | 576 |
| gcc cgg gcg cgc gcc aag gcc gag cgg gag aat gca gac atc atc cgc<br>Ala Arg Ala Arg Ala Lys Ala Glu Arg Glu Asn Ala Asp Ile Ile Arg<br>                 195                  200                205 | | 624 |
| gag cag atc cgc ctg aag gcg gcc gag cac cgt cag acc gtc ttg gag<br>Glu Gln Ile Arg Leu Lys Ala Ala Glu His Arg Gln Thr Val Leu Glu<br>210                     215                  220 | | 672 |
| tcc atc agg acg gct ggc acc ttg ttt ggg gaa gga ttc cgt gcc ttt<br>Ser Ile Arg Thr Ala Gly Thr Leu Phe Gly Glu Gly Phe Arg Ala Phe<br>225                     230                  235                240 | | 720 |
| gtg aca gac tgg gac aaa gtg aca gcc acg gtg gct ggg ctg acg ctg<br>Val Thr Asp Trp Asp Lys Val Thr Ala Thr Val Ala Gly Leu Thr Leu<br>                 245                  250                255 | | 768 |
| ctg gct gtt ggg gtc tac tca gcc aag aat gcc acg ctt gtc gcc ggc<br>Leu Ala Val Gly Val Tyr Ser Ala Lys Asn Ala Thr Leu Val Ala Gly<br>        260                  265                270 | | 816 |
| cgc ttc atc gag gct cgg ctg ggg aag ccg tcc cta gtg agg gag acg<br>Arg Phe Ile Glu Ala Arg Leu Gly Lys Pro Ser Leu Val Arg Glu Thr<br>                 275                  280                285 | | 864 |
| tcc cgc atc acg gtg ctt gag gcg ctg cgg cac ccc atc cag gtc agc<br>Ser Arg Ile Thr Val Leu Glu Ala Leu Arg His Pro Ile Gln Val Ser<br>290                     295                  300 | | 912 |
| cgg cgg ctc ctc agt cga ccc cag gac gcg ctg gag ggt gtt gtg ctc<br>Arg Arg Leu Leu Ser Arg Pro Gln Asp Ala Leu Glu Gly Val Val Leu<br>305                     310                  315                320 | | 960 |
| agt ccc agc ctg gaa gca cgg gtg cgc gac atc gcc ata gca aca agg<br>Ser Pro Ser Leu Glu Ala Arg Val Arg Asp Ile Ala Ile Ala Thr Arg<br>                 325                  330                335 | | 1008 |

```
aac acc aag aag aac cgc agc ctg tac agg aac atc ctg atg tac ggg    1056
Asn Thr Lys Lys Asn Arg Ser Leu Tyr Arg Asn Ile Leu Met Tyr Gly
            340                 345                 350 cca cca ggc acc ggg aag acg ctg ttt gcc aag aaa ctc gcc ctg cac    1104
Pro Pro Gly Thr Gly Lys Thr Leu Phe Ala Lys Lys Leu Ala Leu His
        355                 360                 365 tca ggc atg gac tac gcc atc atg aca ggc ggg gac gtg gcc ccc atg    1152
Ser Gly Met Asp Tyr Ala Ile Met Thr Gly Gly Asp Val Ala Pro Met
    370                 375                 380 ggg cgg gaa ggc gtg acc gcc atg cac aag ctc ttt gac tgg gcc aat    1200
Gly Arg Glu Gly Val Thr Ala Met His Lys Leu Phe Asp Trp Ala Asn
385                 390                 395                 400 acc agc cgg cgc ggc ctc ctg ctc ttt gtg gat gaa gcg gac gcc ttc    1248
Thr Ser Arg Arg Gly Leu Leu Leu Phe Val Asp Glu Ala Asp Ala Phe
                405                 410                 415 ctt cgg aag cga gcc acc gag aag ata agc gag gac ctc agg gcc aca    1296
Leu Arg Lys Arg Ala Thr Glu Lys Ile Ser Glu Asp Leu Arg Ala Thr
            420                 425                 430 ctg aac gcc ttc ctg tac cgc acg ggc cag cac agc aac aag ttc atg    1344
Leu Asn Ala Phe Leu Tyr Arg Thr Gly Gln His Ser Asn Lys Phe Met
        435                 440                 445 ctg gtc ctg gcc agc aac caa cca gag cag ttc gac tgg gcc atc aat    1392
Leu Val Leu Ala Ser Asn Gln Pro Glu Gln Phe Asp Trp Ala Ile Asn
    450                 455                 460 gac cgc atc aat gag atg gtc cac ttc gac ctg cca ggg cag gag gaa    1440
Asp Arg Ile Asn Glu Met Val His Phe Asp Leu Pro Gly Gln Glu Glu
465                 470                 475                 480 cgg gag cgc ctg gtg aga atg tat ttt gac aag tat gtt ctt aag ccg    1488
Arg Glu Arg Leu Val Arg Met Tyr Phe Asp Lys Tyr Val Leu Lys Pro
                485                 490                 495 gcc aca gaa gga aag cag cgc ctg aag ctg gcc cag ttt gac tac ggg    1536
Ala Thr Glu Gly Lys Gln Arg Leu Lys Leu Ala Gln Phe Asp Tyr Gly
            500                 505                 510 agg aag tgc tcg gag gtc gct cgg ctg acg gag ggc atg tcg ggc cgg    1584
Arg Lys Cys Ser Glu Val Ala Arg Leu Thr Glu Gly Met Ser Gly Arg
        515                 520                 525 gag atc gct cag ctg gcc gtg tcc tgg cag gcc acg gcg tat gcc tcc    1632
Glu Ile Ala Gln Leu Ala Val Ser Trp Gln Ala Thr Ala Tyr Ala Ser
    530                 535                 540 gag gac ggg gtc ctg acc gag gcc atg atg gac acc cgc gtg caa gat    1680
Glu Asp Gly Val Leu Thr Glu Ala Met Met Asp Thr Arg Val Gln Asp
545                 550                 555                 560 gct gtc cag cag cac cag cag aag atg tgc tgg ctg aag gcg gaa ggg    1728
Ala Val Gln Gln His Gln Gln Lys Met Cys Trp Leu Lys Ala Glu Gly
                565                 570                 575 cct ggg cgt ggg gac gag ccc tcc cca tcc tga                        1761
Pro Gly Arg Gly Asp Glu Pro Ser Pro Ser
            580                 585

<210> SEQ ID NO 6
<211> LENGTH: 586
<212> TYPE: PRT
<213> ORGANISM: Homo sapiens

<400> SEQUENCE: 6

Met Ser Trp Leu Phe Gly Ile Asn Lys Gly Pro Lys Gly Glu Asp Ala
1               5                   10                  15

Gly Pro Pro Pro Pro Leu Pro Pro Ala Gln Pro Gly Ala Glu Gly Gly
            20                  25                  30

Gly Asp Arg Gly Leu Gly Asp Arg Pro Ala Pro Lys Asp Lys Trp Ser
        35                  40                  45
```

```
Asn Phe Asp Pro Thr Gly Leu Glu Arg Ala Ala Lys Ala Ala Arg Glu
     50                  55                  60

Leu Glu His Ser Arg Tyr Ala Lys Asp Ala Leu Asn Leu Ala Gln Met
 65                  70                  75                  80

Gln Glu Gln Thr Leu Gln Leu Glu Gln Gln Ser Lys Leu Lys Glu Tyr
                 85                  90                  95

Glu Ala Ala Val Glu Gln Leu Lys Ser Glu Gln Ile Arg Ala Gln Ala
                100                 105                 110

Glu Glu Arg Arg Lys Thr Leu Ser Glu Glu Thr Arg Gln His Gln Ala
            115                 120                 125

Arg Ala Gln Tyr Gln Asp Lys Leu Ala Arg Gln Arg Tyr Glu Asp Gln
        130                 135                 140

Leu Lys Gln Gln Gln Leu Leu Asn Glu Glu Asn Leu Arg Lys Gln Glu
145                 150                 155                 160

Glu Ser Val Gln Lys Gln Glu Ala Met Arg Arg Ala Thr Val Glu Arg
                165                 170                 175

Glu Met Glu Leu Arg His Lys Asn Glu Met Leu Arg Val Glu Ala Glu
            180                 185                 190

Ala Arg Ala Arg Ala Lys Ala Glu Arg Glu Asn Ala Asp Ile Ile Arg
        195                 200                 205

Glu Gln Ile Arg Leu Lys Ala Ala Glu His Arg Gln Thr Val Leu Glu
210                 215                 220

Ser Ile Arg Thr Ala Gly Thr Leu Phe Gly Glu Gly Phe Arg Ala Phe
225                 230                 235                 240

Val Thr Asp Trp Asp Lys Val Thr Ala Thr Val Ala Gly Leu Thr Leu
                245                 250                 255

Leu Ala Val Gly Val Tyr Ser Ala Lys Asn Ala Thr Leu Val Ala Gly
            260                 265                 270

Arg Phe Ile Glu Ala Arg Leu Gly Lys Pro Ser Leu Val Arg Glu Thr
        275                 280                 285

Ser Arg Ile Thr Val Leu Glu Ala Leu Arg His Pro Ile Gln Val Ser
290                 295                 300

Arg Arg Leu Leu Ser Arg Pro Gln Asp Ala Leu Glu Gly Val Val Leu
305                 310                 315                 320

Ser Pro Ser Leu Glu Ala Arg Val Arg Asp Ile Ala Ile Ala Thr Arg
                325                 330                 335

Asn Thr Lys Lys Asn Arg Ser Leu Tyr Arg Asn Ile Leu Met Tyr Gly
            340                 345                 350

Pro Pro Gly Thr Gly Lys Thr Leu Phe Ala Lys Lys Leu Ala Leu His
        355                 360                 365

Ser Gly Met Asp Tyr Ala Ile Met Thr Gly Gly Asp Val Ala Pro Met
370                 375                 380

Gly Arg Glu Gly Val Thr Ala Met His Lys Leu Phe Asp Trp Ala Asn
385                 390                 395                 400

Thr Ser Arg Arg Gly Leu Leu Leu Phe Val Asp Glu Ala Asp Ala Phe
                405                 410                 415

Leu Arg Lys Arg Ala Thr Glu Lys Ile Ser Glu Asp Leu Arg Ala Thr
            420                 425                 430

Leu Asn Ala Phe Leu Tyr Arg Thr Gly Gln His Ser Asn Lys Phe Met
        435                 440                 445

Leu Val Leu Ala Ser Asn Gln Pro Glu Gln Phe Asp Trp Ala Ile Asn
450                 455                 460

Asp Arg Ile Asn Glu Met Val His Phe Asp Leu Pro Gly Gln Glu Glu
```

```
                    465                 470                 475                 480
Arg Glu Arg Leu Val Arg Met Tyr Phe Asp Lys Tyr Val Leu Lys Pro
                        485                 490                 495

Ala Thr Glu Gly Lys Gln Arg Leu Lys Leu Ala Gln Phe Asp Tyr Gly
                500                 505                 510

Arg Lys Cys Ser Glu Val Ala Arg Leu Thr Glu Gly Met Ser Gly Arg
            515                 520                 525

Glu Ile Ala Gln Leu Ala Val Ser Trp Gln Ala Thr Ala Tyr Ala Ser
        530                 535                 540

Glu Asp Gly Val Leu Thr Glu Ala Met Met Asp Thr Arg Val Gln Asp
545                 550                 555                 560

Ala Val Gln Gln His Gln Gln Lys Met Cys Trp Leu Lys Ala Glu Gly
                565                 570                 575

Pro Gly Arg Gly Asp Glu Pro Ser Pro Ser
                580                 585

<210> SEQ ID NO 7
<211> LENGTH: 100
<212> TYPE: PRT
<213> ORGANISM: Artificial sequence
<220> FEATURE:
<223> OTHER INFORMATION: Variable light chain SC02-401

<400> SEQUENCE: 7

Thr Gln Ser Pro Ser Ser Leu Ser Ala Ser Val Gly Asp Arg Val Thr
1               5                   10                  15

Ile Thr Cys Arg Ala Ser Gln Ser Ile Ser Ser Tyr Leu Asn Trp Tyr
            20                  25                  30

Gln Gln Lys Pro Gly Lys Ala Pro Lys Leu Leu Ile Tyr Ala Ala Ser
        35                  40                  45

Ser Leu Gln Ser Gly Val Pro Ser Arg Phe Ser Gly Ser Gly Ser Gly
    50                  55                  60

Thr Asp Phe Thr Leu Thr Ile Ser Ser Leu Gln Pro Glu Asp Phe Ala
65                  70                  75                  80

Thr Tyr Tyr Cys Gln Gln Ser Tyr Ser Thr Pro Pro Thr Phe Gly Gln
                85                  90                  95

Gly Thr Lys Val
            100

<210> SEQ ID NO 8
<211> LENGTH: 100
<212> TYPE: PRT
<213> ORGANISM: Artificial sequence
<220> FEATURE:
<223> OTHER INFORMATION: Variable light chain SC02-361

<400> SEQUENCE: 8

Thr Gln Ser Pro Ser Ser Leu Ser Ala Ser Val Gly Asp Arg Val Thr
1               5                   10                  15

Ile Thr Cys Arg Ala Ser Gln Ser Ile Ser Ser Tyr Leu Asn Trp Tyr
            20                  25                  30

Gln Gln Lys Pro Gly Lys Ala Pro Lys Leu Leu Ile Tyr Ala Ala Ser
        35                  40                  45

Ser Leu Gln Ser Gly Val Pro Ser Arg Phe Ser Gly Ser Gly Ser Gly
    50                  55                  60

Thr Asp Phe Thr Leu Thr Ile Ser Ser Leu Gln Pro Glu Asp Phe Ala
65                  70                  75                  80

Thr Tyr Tyr Cys Gln Gln Ser Tyr Ser Thr Pro Pro Thr Phe Gly Gln
```

Gly Thr Lys Val
        100

<210> SEQ ID NO 9
<211> LENGTH: 363
<212> TYPE: DNA
<213> ORGANISM: Artificial sequence
<220> FEATURE:
<223> OTHER INFORMATION: Variable heavy chain SC02-401

<400> SEQUENCE: 9

```
gaggtgcagc tggtggagtc tgggggaggc ttagttcagc ctggggggtc cctgagactc    60
tcctgtgcag cctctggatt caccttcagt agctactgga tgcactgggt ccgccaagct   120
ccagggaagg ggctggtgtg gtctcacgt attaatagtg atgggagtag cacaagctac    180
gcggactccg tgaagggccg attcaccatc tccagagaca cgccaagaa cacgctgtat    240
ctgcaaatga acagtctgag agccgaggac acggccgtgt attactgtgc aagagacgac    300
actcctacgt ctgattacgg gtttgactcc tggggccagg caccctggt gaccgtctcc    360
agc                                                                  363
```

<210> SEQ ID NO 10
<211> LENGTH: 354
<212> TYPE: DNA
<213> ORGANISM: Artificial sequence
<220> FEATURE:
<223> OTHER INFORMATION: Variable heavy chain SC02-361

<400> SEQUENCE: 10

```
gaggtgcagc tggtggagtc tgggggaggc ttggtacagc ctggcaggtc cctgagactc    60
tcctgtgcag cctctggatt cacctttgat gattatggca tgagctgggt ccgccaagct   120
ccagggaagg gtctggagtg gtctctctt attagttggg atggtggtag cacatactat    180
gcagactctg tgaagggccg attcaccatc tccagagaca cagcaaaaa ctccctgtat    240
ctgcaaatga acagcctgag agccgaggac acggccgtgt attactgtgc aaagtgggcg    300
ccttcgcatt cctttgacta ctggggccag ggcaccctgg tgaccgtctc cagc          354
```

<210> SEQ ID NO 11
<211> LENGTH: 741
<212> TYPE: DNA
<213> ORGANISM: Artificial sequence
<220> FEATURE:
<223> OTHER INFORMATION: SC02-401
<220> FEATURE:
<221> NAME/KEY: CDS
<222> LOCATION: (1)..(741)
<223> OTHER INFORMATION: Nucleotide sequence encoding SC02-401

<400> SEQUENCE: 11

```
gag gtg cag ctg gtg gag tct ggg gga ggc tta gtt cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agc tac      96
Ser Leu Arg Leu Ser Cys Ala Ala Ser Gly Phe Thr Phe Ser Ser Tyr
            20                  25                  30 tgg atg cac tgg gtc cgc caa gct cca ggg aag ggg ctg gtg tgg gtc     144
Trp Met His Trp Val Arg Gln Ala Pro Gly Lys Gly Leu Val Trp Val
        35                  40                  45 tca cgt att aat agt gat ggg agt agc aca agc tac gcg gac tcc gtg     192
Ser Arg Ile Asn Ser Asp Gly Ser Ser Thr Ser Tyr Ala Asp Ser Val
    50                  55                  60
```

```
aag ggc cga ttc acc atc tcc aga gac aac gcc aag aac acg ctg tat         240
Lys Gly Arg Phe Thr Ile Ser Arg Asp Asn Ala Lys Asn Thr Leu Tyr
 65                  70                  75                  80 ctg caa atg aac agt ctg aga gcc gag gac acg gcc gtg tat tac tgt         288
Leu Gln Met Asn Ser Leu Arg Ala Glu Asp Thr Ala Val Tyr Tyr Cys
                 85                  90                  95 gca aga gac gac act cct acg tct gat tac ggg ttt gac tcc tgg ggc         336
Ala Arg Asp Asp Thr Pro Thr Ser Asp Tyr Gly Phe Asp Ser Trp Gly
            100                 105                 110 caa ggt acc ctg gtc acc gtc tcg agt ggt gga ggt tca ggc gga              384
Gln Gly Thr Leu Val Thr Val Ser Ser Gly Gly Gly Ser Gly Gly
        115                 120                 125 ggt ggc tct ggc ggt ggc gga tcg gaa att gag ctc acc cag tct cca         432
Gly Gly Ser Gly Gly Gly Gly Ser Glu Ile Glu Leu Thr Gln Ser Pro
        130                 135                 140 tcc tcc ctg tct gca tct gta gga gac aga gtc acc atc act tgc cgg         480
Ser Ser Leu Ser Ala Ser Val Gly Asp Arg Val Thr Ile Thr Cys Arg
145                 150                 155                 160 gca agt cag agc att agc agc tac tta aat tgg tat cag cag aaa cca         528
Ala Ser Gln Ser Ile Ser Ser Tyr Leu Asn Trp Tyr Gln Gln Lys Pro
                165                 170                 175 ggg aaa gcc cct aag ctc ctg atc tat gct gca tcc agt ttg caa agt         576
Gly Lys Ala Pro Lys Leu Leu Ile Tyr Ala Ala Ser Ser Leu Gln Ser
            180                 185                 190 ggg gtc cca tca agg ttc agt ggc agt gga tct ggg aca gat ttc act         624
Gly Val Pro Ser Arg Phe Ser Gly Ser Gly Ser Gly Thr Asp Phe Thr
        195                 200                 205 ctc acc atc agc agt ctg caa cct gaa gat ttt gca act tac tac tgt         672
Leu Thr Ile Ser Ser Leu Gln Pro Glu Asp Phe Ala Thr Tyr Tyr Cys
    210                 215                 220 caa cag agt tac agt acc cct cca acg ttc ggc caa ggg acc aag gtg         720
Gln Gln Ser Tyr Ser Thr Pro Pro Thr Phe Gly Gln Gly Thr Lys Val
225                 230                 235                 240 gag atc aaa cgt gcg gcc gca                                              741
Glu Ile Lys Arg Ala Ala Ala
                245

<210> SEQ ID NO 12
<211> LENGTH: 247
<212> TYPE: PRT
<213> ORGANISM: Artificial sequence
<220> FEATURE:
<223> OTHER INFORMATION: SC02-401

<400> SEQUENCE: 12

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Thr Pro Thr Ser Asp Tyr Gly Phe Asp Ser Trp Gly
            100                 105                 110
```

```
Gln Gly Thr Leu Val Thr Val Ser Ser Gly Gly Gly Ser Gly Gly
            115                 120                 125

Gly Gly Ser Gly Gly Gly Ser Glu Ile Glu Leu Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Tyr Cys
        210                 215                 220

Gln Gln Ser Tyr Ser Thr Pro Pro Thr Phe Gly Gln Gly Thr Lys Val
225                 230                 235                 240

Glu Ile Lys Arg Ala Ala Ala
                245
```

<210> SEQ ID NO 13
<211> LENGTH: 732
<212> TYPE: DNA
<213> ORGANISM: Artificial sequence
<220> FEATURE:
<223> OTHER INFORMATION: SC02-361
<220> FEATURE:
<221> NAME/KEY: CDS
<222> LOCATION: (1)..(732)
<223> OTHER INFORMATION: Nucleotide sequence encoding SC02-361

<400> SEQUENCE: 13

```
gag gtg cag ctg gtg gag tct ggg gga ggc ttg gta cag cct ggc agg      48
Glu Val Gln Leu Val Glu Ser Gly Gly Gly Leu Val Gln Pro Gly Arg
1               5                   10                  15 tcc ctg aga ctc tcc tgt gca gcc tct gga ttc acc ttt gat gat tat      96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggt ctg gag tgg gtc     144
Gly Met Ser Trp Val Arg Gln Ala Pro Gly Lys Gly Leu Glu Trp Val
        35                  40                  45 tct ctt att agt tgg gat ggt ggt agc aca tac tat gca gac tct gtg     192
Ser Leu Ile Ser Trp Asp Gly Gly Ser Thr Tyr Tyr Ala Asp Ser Val
    50                  55                  60 aag ggc cga ttc acc atc tcc aga gac aac agc aaa aac tcc ctg tat     240
Lys Gly Arg Phe Thr Ile Ser Arg Asp Asn Ser Lys Asn Ser Leu Tyr
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gca aag tgg gcg cct tcg cat tcc ttt gac tac tgg ggc caa ggt acc     336
Ala Lys Trp Ala Pro Ser His Ser Phe Asp Tyr Trp Gly Gln Gly Thr
            100                 105                 110 ctg gtc acc gtc tcg agt ggt gga ggc ggt tca ggc gga ggt ggc tct     384
Leu Val Thr Val Ser Ser Gly Gly Gly Gly Ser Gly Gly Gly Gly Ser
        115                 120                 125 ggc ggt ggc gga tcg gaa att gag ctc acc cag tct cca tcc tcc ctg     432
Gly Gly Gly Gly Ser Glu Ile Glu Leu Thr Gln Ser Pro Ser Ser Leu
    130                 135                 140 tct gca tct gta gga gac aga gtc acc atc act tgc cgg gca agt cag     480
Ser Ala Ser Val Gly Asp Arg Val Thr Ile Thr Cys Arg Ala Ser Gln
145                 150                 155                 160
```

```
agc att agc agc tac tta aat tgg tat cag cag aaa cca ggg aaa gcc    528
Ser Ile Ser Ser Tyr Leu Asn Trp Tyr Gln Gln Lys Pro Gly Lys Ala
            165                 170                 175 cct aag ctc ctg atc tat gct gca tcc agt ttg caa agt ggg gtc cca    576
Pro Lys Leu Leu Ile Tyr Ala Ala Ser Ser Leu Gln Ser Gly Val Pro
        180                 185                 190 tca agg ttc agt ggc agt gga tct ggg aca gat ttc act ctc acc atc    624
Ser Arg Phe Ser Gly Ser Gly Ser Gly Thr Asp Phe Thr Leu Thr Ile
    195                 200                 205 agc agt ctg caa cct gaa gat ttt gca act tac tac tgt caa cag agt    672
Ser Ser Leu Gln Pro Glu Asp Phe Ala Thr Tyr Tyr Cys Gln Gln Ser
210                 215                 220 tac agt acc cct cca acg ttc ggc caa ggg acc aag gtg gag atc aaa    720
Tyr Ser Thr Pro Pro Thr Phe Gly Gln Gly Thr Lys Val Glu Ile Lys
225                 230                 235                 240 cgt gcg gcc gca                                                    732
Arg Ala Ala Ala <210> SEQ ID NO 14
<211> LENGTH: 244
<212> TYPE: PRT
<213> ORGANISM: Artificial sequence
<220> FEATURE:
<223> OTHER INFORMATION: SC02-361

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Trp Ala Pro Ser His Ser Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
    210                 215                 220

Tyr Ser Thr Pro Pro Thr Phe Gly Gln Gly Thr Lys Val Glu Ile Lys
225                 230                 235                 240

Arg Ala Ala Ala
```

<210> SEQ ID NO 15
<211> LENGTH: 55
<212> TYPE: DNA
<213> ORGANISM: Artificial sequence
<220> FEATURE:
<223> OTHER INFORMATION: Oligonucleotide 5K-C

<400> SEQUENCE: 15
acctgtctcg agtttccat ggctgacatc cagatgaccc agtctccatc ctccc         55

<210> SEQ ID NO 16
<211> LENGTH: 55
<212> TYPE: DNA
<213> ORGANISM: Artificial sequence
<220> FEATURE:
<223> OTHER INFORMATION: Oligonucleotide 3K-C

<400> SEQUENCE: 16
caagggacca aggtggagat caaacgtaag tgcactttgc ggccgctaag gaaaa         55

<210> SEQ ID NO 17
<211> LENGTH: 46
<212> TYPE: DNA
<213> ORGANISM: Artificial sequence
<220> FEATURE:
<223> OTHER INFORMATION: Oligonucleotide 5H-B

<400> SEQUENCE: 17
acctgtcttg aattctccat ggccgaggtg cagctggtgg agtctg              46

<210> SEQ ID NO 18
<211> LENGTH: 47
<212> TYPE: DNA
<213> ORGANISM: Artificial sequence
<220> FEATURE:
<223> OTHER INFORMATION: Oligonucleotide Sy3H-a reversed

<400> SEQUENCE: 18
ggggccaggg caccctggtg accgtctcca gcgctagcac caagggc             47

<210> SEQ ID NO 19
<211> LENGTH: 1353
<212> TYPE: DNA
<213> ORGANISM: Artificial sequence
<220> FEATURE:
<223> OTHER INFORMATION: Heavy chain CR2401
<220> FEATURE:
<221> NAME/KEY: CDS
<222> LOCATION: (1)..(1353)
<223> OTHER INFORMATION: Nucleotide sequence encoding heavy chain

<400> SEQUENCE: 19

| gag | gtg | cag | ctg | gtg | gag | tct | ggg | gga | ggc | tta | gtt | cag | cct | ggg | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttc | agt | agc | tac | 96 |
| Ser | Leu | Arg | Leu | Ser | Cys | Ala | Ala | Ser | Gly | Phe | Thr | Phe | Ser | Ser | Tyr | |
| | | 20 | | | | | 25 | | | | | 30 | | | | |

| tgg | atg | cac | tgg | gtc | cgc | caa | gct | cca | ggg | aag | ggg | ctg | gtg | tgg | gtc | 144 |
| Trp | Met | His | Trp | Val | Arg | Gln | Ala | Pro | Gly | Lys | Gly | Leu | Val | Trp | Val | |
| | | | 35 | | | | | 40 | | | | | 45 | | | |

| tca | cgt | att | aat | agt | gat | ggg | agt | agc | aca | agc | tac | gcg | gac | tcc | gtg | 192 |
| Ser | Arg | Ile | Asn | Ser | Asp | Gly | Ser | Ser | Thr | Ser | Tyr | Ala | Asp | Ser | Val | |
| 50 | | | | | 55 | | | | | 60 | | | | | | |

| aag | ggc | cga | ttc | acc | atc | tcc | aga | gac | aac | gcc | aag | aac | acg | ctg | tat | 240 |

```
Lys Gly Arg Phe Thr Ile Ser Arg Asp Asn Ala Lys Asn Thr Leu Tyr
 65                  70                  75                  80 ctg caa atg aac agt ctg aga gcc gag gac acg gcc gtg tat tac tgt      288
Leu Gln Met Asn Ser Leu Arg Ala Glu Asp Thr Ala Val Tyr Tyr Cys
                 85                  90                  95 gca aga gac gac act cct acg tct gat tac ggg ttt gac tcc tgg ggc      336
Ala Arg Asp Asp Thr Pro Thr Ser Asp Tyr Gly Phe Asp Ser Trp Gly
            100                 105                 110 cag ggc acc ctg gtg acc gtc tcc agc gct agc acc aag ggc ccc agc      384
Gln Gly Thr Leu Val Thr Val Ser Ser Ala Ser Thr Lys Gly Pro Ser
        115                 120                 125 gtg ttc ccc ctg gcc ccc agc agc aag agc acc agc ggc ggc aca gcc      432
Val Phe Pro Leu Ala Pro Ser Ser Lys Ser Thr Ser Gly Gly Thr Ala
    130                 135                 140 gcc ctg ggc tgc ctg gtg aag gac tac ttc ccc gag ccc gtg acc gtg      480
Ala Leu Gly Cys Leu Val Lys Asp Tyr Phe Pro Glu Pro Val Thr Val
145                 150                 155                 160 agc tgg aac agc ggc gcc ttg acc agc ggc gtg cac acc ttc ccc gcc      528
Ser Trp Asn Ser Gly Ala Leu Thr Ser Gly Val His Thr Phe Pro Ala
                165                 170                 175 gtg ctg cag agc agc ggc ctg tac agc ctg agc agc gtg gtg acc gtg      576
Val Leu Gln Ser Ser Gly Leu Tyr Ser Leu Ser Ser Val Val Thr Val
            180                 185                 190 ccc agc agc agc ctg ggc acc cag acc tac atc tgc aac gtg aac cac      624
Pro Ser Ser Ser Leu Gly Thr Gln Thr Tyr Ile Cys Asn Val Asn His
        195                 200                 205 aag ccc agc aac acc aag gtg gac aaa cgc gtg gag ccc aag agc tgc      672
Lys Pro Ser Asn Thr Lys Val Asp Lys Arg Val Glu Pro Lys Ser Cys
    210                 215                 220 gac aag acc cac acc tgc ccc ccc tgc cct gcc ccc gag ctg ctg ggc      720
Asp Lys Thr His Thr Cys Pro Pro Cys Pro Ala Pro Glu Leu Leu Gly
225                 230                 235                 240 gga ccc tcc gtg ttc ctg ttc ccc ccc aag ccc aag gac acc ctc atg      768
Gly Pro Ser Val Phe Leu Phe Pro Pro Lys Pro Lys Asp Thr Leu Met
                245                 250                 255 atc agc cgg acc ccc gag gtg acc tgc gtg gtg gtg gac gtg agc cac      816
Ile Ser Arg Thr Pro Glu Val Thr Cys Val Val Val Asp Val Ser His
            260                 265                 270 gag gac ccc gag gtg aag ttc aac tgg tac gtg gac ggc gtg gag gtg      864
Glu Asp Pro Glu Val Lys Phe Asn Trp Tyr Val Asp Gly Val Glu Val
        275                 280                 285 cac aac gcc aag acc aag ccc cgg gag gag cag tac aac agc acc tac      912
His Asn Ala Lys Thr Lys Pro Arg Glu Glu Gln Tyr Asn Ser Thr Tyr
    290                 295                 300 cgg gtg gtg agc gtg ctc acc gtg ctg cac cag gac tgg ctg aac ggc      960
Arg Val Val Ser Val Leu Thr Val Leu His Gln Asp Trp Leu Asn Gly
305                 310                 315                 320 aag gag tac aag tgc aag gtg agc aac aag gcc ctg cct gcc ccc atc     1008
Lys Glu Tyr Lys Cys Lys Val Ser Asn Lys Ala Leu Pro Ala Pro Ile
                325                 330                 335 gag aag acc atc agc aag gcc aag ggc cag ccc cgg gag ccc cag gtg     1056
Glu Lys Thr Ile Ser Lys Ala Lys Gly Gln Pro Arg Glu Pro Gln Val
            340                 345                 350 tac acc ctg ccc ccc agc cgg gag gag atg acc aag aac cag gtg tcc     1104
Tyr Thr Leu Pro Pro Ser Arg Glu Glu Met Thr Lys Asn Gln Val Ser
        355                 360                 365 ctc acc tgt ctg gtg aag ggc ttc tac ccc agc gac atc gcc gtg gag     1152
Leu Thr Cys Leu Val Lys Gly Phe Tyr Pro Ser Asp Ile Ala Val Glu
    370                 375                 380 tgg gag agc aac ggc cag ccc gag aac aac tac aag acc acc ccc cct     1200
```

```
Trp Glu Ser Asn Gly Gln Pro Glu Asn Asn Tyr Lys Thr Thr Pro Pro
385                 390                 395                 400 gtg ctg gac agc gac ggc agc ttc ttc ctg tac agc aag ctc acc gtg      1248
Val Leu Asp Ser Asp Gly Ser Phe Phe Leu Tyr Ser Lys Leu Thr Val
                405                 410                 415 gac aag agc cgg tgg cag cag ggc aac gtc ttc agc tgc agc gtg atg      1296
Asp Lys Ser Arg Trp Gln Gln Gly Asn Val Phe Ser Cys Ser Val Met
            420                 425                 430 cac gag gcc ctg cac aac cac tac acc cag aag agc ctc tcc ctg tct      1344
His Glu Ala Leu His Asn His Tyr Thr Gln Lys Ser Leu Ser Leu Ser
        435                 440                 445 ccc ggc aag                                                          1353
Pro Gly Lys
    450
```

<210> SEQ ID NO 20
<211> LENGTH: 451
<212> TYPE: PRT
<213> ORGANISM: Artificial sequence
<220> FEATURE:
<223> OTHER INFORMATION: Heavy chain CR2401

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Thr Pro Thr Ser Asp Tyr Gly Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 21
<211> LENGTH: 1344
<212> TYPE: DNA
<213> ORGANISM: Artificial sequence
<220> FEATURE:
<223> OTHER INFORMATION: Heavy chain CR2361
<220> FEATURE:
<221> NAME/KEY: CDS
<222> LOCATION: (1)..(1344)
<223> OTHER INFORMATION: Nucleotide sequence encoding heavy chain

<400> SEQUENCE: 21 gag gtg cag ctg gtg gag tct ggg gga ggc ttg gta cag cct ggc agg      48
Glu Val Gln Leu Val Glu Ser Gly Gly Gly Leu Val Gln Pro Gly Arg
1               5                   10                  15 tcc ctg aga ctc tcc tgt gca gcc tct gga ttc acc ttt gat gat tat      96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggt ctg gag tgg gtc     144
Gly Met Ser Trp Val Arg Gln Ala Pro Gly Lys Gly Leu Glu Trp Val
        35                  40                  45 tct ctt att agt tgg gat ggt ggt agc aca tac tat gca gac tct gtg     192
Ser Leu Ile Ser Trp Asp Gly Gly Ser Thr Tyr Tyr Ala Asp Ser Val
    50                  55                  60 aag ggc cga ttc acc atc tcc aga gac aac agc aaa aac tcc ctg tat     240
Lys Gly Arg Phe Thr Ile Ser Arg Asp Asn Ser Lys Asn Ser Leu Tyr
65                  70                  75                  80 ctg caa atg aac agc ctg aga gcc gag gac acg gcc gtg tat tac tgt     288
Leu Gln Met Asn Ser Leu Arg Ala Glu Asp Thr Ala Val Tyr Tyr Cys
                85                  90                  95 gca aag tgg gcg cct tcg cat tcc ttt gac tac tgg ggc cag ggc acc     336
Ala Lys Trp Ala Pro Ser His Ser Phe Asp Tyr Trp Gly Gln Gly Thr
            100                 105                 110 ctg gtg acc gtc tcc agc gct agc acc aag ggc ccc agc gtg ttc ccc     384
Leu Val Thr Val Ser Ser Ala Ser Thr Lys Gly Pro Ser Val Phe Pro
```

-continued

```
             115                 120                 125
ctg gcc ccc agc agc aag agc acc agc ggc ggc aca gcc gcc ctg ggc    432
Leu Ala Pro Ser Ser Lys Ser Thr Ser Gly Gly Thr Ala Ala Leu Gly
        130                 135                 140 tgc ctg gtg aag gac tac ttc ccc gag ccc gtg acc gtg agc tgg aac    480
Cys Leu Val Lys Asp Tyr Phe Pro Glu Pro Val Thr Val Ser Trp Asn
145                 150                 155                 160 agc ggc gcc ttg acc agc ggc gtg cac acc ttc ccc gcc gtg ctg cag    528
Ser Gly Ala Leu Thr Ser Gly Val His Thr Phe Pro Ala Val Leu Gln
                165                 170                 175 agc agc ggc ctg tac agc ctg agc agc gtg gtg acc gtg ccc agc agc    576
Ser Ser Gly Leu Tyr Ser Leu Ser Ser Val Val Thr Val Pro Ser Ser
            180                 185                 190 agc ctg ggc acc cag acc tac atc tgc aac gtg aac cac aag ccc agc    624
Ser Leu Gly Thr Gln Thr Tyr Ile Cys Asn Val Asn His Lys Pro Ser
        195                 200                 205 aac acc aag gtg gac aaa cgc gtg gag ccc aag agc tgc gac aag acc    672
Asn Thr Lys Val Asp Lys Arg Val Glu Pro Lys Ser Cys Asp Lys Thr
210                 215                 220 cac acc tgc ccc ccc tgc cct gcc ccc gag ctg ctg ggc gga ccc tcc    720
His Thr Cys Pro Pro Cys Pro Ala Pro Glu Leu Leu Gly Gly Pro Ser
225                 230                 235                 240 gtg ttc ctg ttc ccc ccc aag ccc aag gac acc ctc atg atc agc cgg    768
Val Phe Leu Phe Pro Pro Lys Pro Lys Asp Thr Leu Met Ile Ser Arg
                245                 250                 255 acc ccc gag gtg acc tgc gtg gtg gtg gac gtg agc cac gag gac ccc    816
Thr Pro Glu Val Thr Cys Val Val Val Asp Val Ser His Glu Asp Pro
            260                 265                 270 gag gtg aag ttc aac tgg tac gtg gac ggc gtg gag gtg cac aac gcc    864
Glu Val Lys Phe Asn Trp Tyr Val Asp Gly Val Glu Val His Asn Ala
        275                 280                 285 aag acc aag ccc cgg gag gag cag tac aac agc acc tac cgg gtg gtg    912
Lys Thr Lys Pro Arg Glu Glu Gln Tyr Asn Ser Thr Tyr Arg Val Val
290                 295                 300 agc gtg ctc acc gtg ctg cac cag gac tgg ctg aac ggc aag gag tac    960
Ser Val Leu Thr Val Leu His Gln Asp Trp Leu Asn Gly Lys Glu Tyr
305                 310                 315                 320 aag tgc aag gtg agc aac aag gcc ctg cct gcc ccc atc gag aag acc   1008
Lys Cys Lys Val Ser Asn Lys Ala Leu Pro Ala Pro Ile Glu Lys Thr
                325                 330                 335 atc agc aag gcc aag ggc cag ccc cgg gag ccc cag gtg tac acc ctg   1056
Ile Ser Lys Ala Lys Gly Gln Pro Arg Glu Pro Gln Val Tyr Thr Leu
            340                 345                 350 ccc ccc agc cgg gag gag atg acc aag aac cag gtg tcc ctc acc tgt   1104
Pro Pro Ser Arg Glu Glu Met Thr Lys Asn Gln Val Ser Leu Thr Cys
        355                 360                 365 ctg gtg aag ggc ttc tac ccc agc gac atc gcc gtg gag tgg gag agc   1152
Leu Val Lys Gly Phe Tyr Pro Ser Asp Ile Ala Val Glu Trp Glu Ser
370                 375                 380 aac ggc cag ccc gag aac aac tac aag acc acc ccc cct gtg ctg gac   1200
Asn Gly Gln Pro Glu Asn Asn Tyr Lys Thr Thr Pro Pro Val Leu Asp
385                 390                 395                 400 agc gac ggc agc ttc ttc ctg tac agc aag ctc acc gtg gac aag agc   1248
Ser Asp Gly Ser Phe Phe Leu Tyr Ser Lys Leu Thr Val Asp Lys Ser
                405                 410                 415 cgg tgg cag cag ggc aac gtg ttc agc tgc agc gtg atg cac gag gcc   1296
Arg Trp Gln Gln Gly Asn Val Phe Ser Cys Ser Val Met His Glu Ala
            420                 425                 430 ctg cac aac cac tac acc cag aag agc ctg agc ctg agc ccc ggc aag   1344
Leu His Asn His Tyr Thr Gln Lys Ser Leu Ser Leu Ser Pro Gly Lys
```

<210> SEQ ID NO 22
<211> LENGTH: 448
<212> TYPE: PRT
<213> ORGANISM: Artificial sequence
<220> FEATURE:
<223> OTHER INFORMATION: Heavy chain CR2361

<400> SEQUENCE: 22

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Trp Ala Pro Ser His Ser Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

-continued

```
Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385                 390             395                 400

Ser Asp Gly Ser Phe Phe Leu Tyr Ser Lys Leu Thr Val Asp Lys Ser
                405             410                 415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
        435             440             445
```

<210> SEQ ID NO 23
<211> LENGTH: 642
<212> TYPE: DNA
<213> ORGANISM: Artificial sequence
<220> FEATURE:
<223> OTHER INFORMATION: Light chain CR2401
<220> FEATURE:
<221> NAME/KEY: CDS
<222> LOCATION: (1)..(642)
<223> OTHER INFORMATION: Nucleotide sequence encoding light chain

<400> SEQUENCE: 23

```
gac att cag atg acc cag tct cca tcc tcc ctg tct gca tct gta gga        48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac        96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc      144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc      192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct      240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa cgg acc gtg gcc gct      336
Thr Phe Gly Gln Gly Thr Lys Val Glu Ile Lys Arg Thr Val Ala Ala
            100                 105                 110 ccc agc gtg ttc atc ttc ccc ccc tcc gac gag cag ctg aag agc ggc      384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccc cgg gag gcc      432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac agc cag      480
Lys Val Gln Trp Lys Val Asp Asn Ala Leu Gln Ser Gly Asn Ser Gln
145                 150                 155                 160 gag agc gtg acc gag cag gac agc aag gac tcc acc tac agc ctg agc      528
Glu Ser Val Thr Glu Gln Asp Ser Lys Asp Ser Thr Tyr Ser Leu Ser
                165                 170                 175 agc acc ctc acc ctg agc aag gcc gac tac gag aag cac aag gtg tac      576
Ser Thr Leu Thr Leu Ser Lys Ala Asp Tyr Glu Lys His Lys Val Tyr
            180                 185                 190 gcc tgc gag gtg acc cac cag ggc ctg agc agc ccc gtg acc aag agc      624
Ala Cys Glu Val Thr His Gln Gly Leu Ser Ser Pro Val Thr Lys Ser
```

```
                    195                 200                 205
ttc aac cgg ggc gag tgt                                                642
Phe Asn Arg Gly Glu Cys
    210

<210> SEQ ID NO 24
<211> LENGTH: 214
<212> TYPE: PRT
<213> ORGANISM: Artificial sequence
<220> FEATURE:
<223> OTHER INFORMATION: Light chain CR2401

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 642
<212> TYPE: DNA
<213> ORGANISM: Artificial sequence
<220> FEATURE:
<223> OTHER INFORMATION: Light chain CR2361
<220> FEATURE:
<221> NAME/KEY: CDS
<222> LOCATION: (1)..(642)
<223> OTHER INFORMATION: Nucleotide sequence encoding light chain

<400> SEQUENCE: 25 gac att cag atg acc cag tct cca tcc tcc ctg tct gca tct gta gga     48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac     96
Asp Arg Val Thr Ile Thr Cys Arg Ala Ser Gln Ser Ile Ser Ser Tyr
            20                  25                  30
```

```
tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
 50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa cgg acc gtg gcc gct     336
Thr Phe Gly Gln Gly Thr Lys Val Glu Ile Lys Arg Thr Val Ala Ala
            100                 105                 110 ccc agc gtg ttc atc ttc ccc ccc tcc gac gag cag ctg aag agc ggc     384
Pro Ser Val Phe Ile Phe Pro Pro Ser Asp Glu Gln Leu Lys Ser Gly
            115                 120                 125 acc gcc agc gtg gtg tgc ctg ctg aac aac ttc tac ccc cgg gag gcc     432
Thr Ala Ser Val Val Cys Leu Leu Asn Asn Phe Tyr Pro Arg Glu Ala
130                 135                 140 aag gtg cag tgg aag gtg gac aac gcc ctg cag agc ggc aac agc cag     480
Lys Val Gln Trp Lys Val Asp Asn Ala Leu Gln Ser Gly Asn Ser Gln
145                 150                 155                 160 gag agc gtg acc gag cag gac agc aag gac tcc acc tac agc ctg agc     528
Glu Ser Val Thr Glu Gln Asp Ser Lys Asp Ser Thr Tyr Ser Leu Ser
                165                 170                 175 agc acc ctc acc ctg agc aag gcc gac tac gag aag cac aag gtg tac     576
Ser Thr Leu Thr Leu Ser Lys Ala Asp Tyr Glu Lys His Lys Val Tyr
            180                 185                 190 gcc tgc gag gtg acc cac cag ggc ctg agc agc ccc gtg acc aag agc     624
Ala Cys Glu Val Thr His Gln Gly Leu Ser Ser Pro Val Thr Lys Ser
            195                 200                 205 ttc aac cgg ggc gag tgt                                              642
Phe Asn Arg Gly Glu Cys
    210

<210> SEQ ID NO 26
<211> LENGTH: 214
<212> TYPE: PRT
<213> ORGANISM: Artificial sequence
<220> FEATURE:
<223> OTHER INFORMATION: Light chain CR2361

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 15
<212> TYPE: PRT
<213> ORGANISM: Artificial sequence
<220> FEATURE:
<223> OTHER INFORMATION: Peptide

<400> SEQUENCE: 27

Phe Glu Val Ile Glu Phe Asp Asp Gly Ala Gly Ser Val Leu Arg
1               5                   10                  15

<210> SEQ ID NO 28
<211> LENGTH: 33
<212> TYPE: PRT
<213> ORGANISM: Artificial sequence
<220> FEATURE:
<223> OTHER INFORMATION: Peptide

<400> SEQUENCE: 28

Ala Ala Gly Thr Glu Gly Pro Phe Gln Glu Val Asp Gly Val Ala Thr
1               5                   10                  15

Thr Arg Tyr Ser Ile Gly Gly Leu Ser Pro Phe Ser Glu Tyr Ala Phe
            20                  25                  30

Arg

<210> SEQ ID NO 29
<211> LENGTH: 11
<212> TYPE: PRT
<213> ORGANISM: Artificial sequence
<220> FEATURE:
<223> OTHER INFORMATION: Peptide

<400> SEQUENCE: 29

Thr Gly Glu Gln Ala Pro Ser Ser Pro Pro Arg
1               5                   10

<210> SEQ ID NO 30
<211> LENGTH: 12
<212> TYPE: PRT
<213> ORGANISM: Artificial sequence
<220> FEATURE:
<223> OTHER INFORMATION: Peptide

<400> SEQUENCE: 30

Ile Gln Leu Ser Trp Leu Leu Pro Pro Gln Glu Arg
1               5                   10

<210> SEQ ID NO 31
<211> LENGTH: 11
```

```
<212> TYPE: PRT
<213> ORGANISM: Artificial sequence
<220> FEATURE:
<223> OTHER INFORMATION: Peptide

<400> SEQUENCE: 31

Val Ser Trp Val Pro Pro Ala Asp Ser Arg
1               5                   10

<210> SEQ ID NO 32
<211> LENGTH: 17
<212> TYPE: PRT
<213> ORGANISM: Artificial sequence
<220> FEATURE:
<223> OTHER INFORMATION: Peptide

<400> SEQUENCE: 32

Ala His Thr Asp Val Gly Pro Gly Pro Glu Ser Ser Pro Val Leu Val
1               5                   10                  15

Arg

<210> SEQ ID NO 33
<211> LENGTH: 9
<212> TYPE: PRT
<213> ORGANISM: Artificial sequence
<220> FEATURE:
<223> OTHER INFORMATION: Peptide

<400> SEQUENCE: 33

Ile Ile Ser Tyr Thr Val Val Phe Arg
1               5

<210> SEQ ID NO 34
<211> LENGTH: 20
<212> TYPE: PRT
<213> ORGANISM: Artificial sequence
<220> FEATURE:
<223> OTHER INFORMATION: Peptide

<400> SEQUENCE: 34

Val Ala Ala Ala Met Lys Thr Ser Val Leu Leu Ser Trp Glu Val Pro
1               5                   10                  15

Asp Ser Tyr Lys
            20

<210> SEQ ID NO 35
<211> LENGTH: 14
<212> TYPE: PRT
<213> ORGANISM: Artificial sequence
<220> FEATURE:
<223> OTHER INFORMATION: Peptide

<400> SEQUENCE: 35

Gly Ser Ser Ala Gly Gly Leu Gln His Leu Val Ser Ile Arg
1               5                   10

<210> SEQ ID NO 36
<211> LENGTH: 11
<212> TYPE: PRT
<213> ORGANISM: Artificial sequence
<220> FEATURE:
<223> OTHER INFORMATION: Peptide

<400> SEQUENCE: 36

Trp Phe Tyr Ile Val Val Val Pro Ile Asp Arg
1               5                   10
```

<210> SEQ ID NO 37
<211> LENGTH: 11
<212> TYPE: PRT
<213> ORGANISM: Artificial sequence
<220> FEATURE:
<223> OTHER INFORMATION: Peptide

<400> SEQUENCE: 37

Tyr Ala Asn Val Ile Ala Tyr Asp His Ser Arg
1               5                   10

<210> SEQ ID NO 38
<211> LENGTH: 30
<212> TYPE: PRT
<213> ORGANISM: Artificial sequence
<220> FEATURE:
<223> OTHER INFORMATION: Peptide

<400> SEQUENCE: 38

Thr Gly Cys Phe Ile Val Ile Asp Ala Met Leu Glu Arg Met Lys His
1               5                   10                  15

Glu Lys Thr Val Asp Ile Tyr Gly His Val Thr Cys Met Arg
            20                  25                  30

<210> SEQ ID NO 39
<211> LENGTH: 10
<212> TYPE: PRT
<213> ORGANISM: Artificial sequence
<220> FEATURE:
<223> OTHER INFORMATION: Peptide

<400> SEQUENCE: 39

Asn Val Leu Glu Leu Ser Asn Val Val Arg
1               5                   10

<210> SEQ ID NO 40
<211> LENGTH: 1897
<212> TYPE: PRT
<213> ORGANISM: Homo sapiens

<400> SEQUENCE: 40

Met Val Pro Leu Val Pro Ala Leu Val Met Leu Gly Leu Val Ala Gly
1               5                   10                  15

Ala His Gly Asp Ser Lys Pro Val Phe Ile Lys Val Pro Glu Asp Gln
            20                  25                  30

Thr Gly Leu Ser Gly Gly Val Ala Ser Phe Val Cys Gln Ala Thr Gly
        35                  40                  45

Glu Pro Lys Pro Arg Ile Thr Trp Met Lys Lys Gly Lys Lys Val Ser
    50                  55                  60

Ser Gln Arg Phe Glu Val Ile Glu Phe Asp Asp Gly Ala Gly Ser Val
65                  70                  75                  80

Leu Arg Ile Gln Pro Leu Arg Val Gln Arg Asp Glu Ala Ile Tyr Glu
                85                  90                  95

Cys Thr Ala Thr Asn Ser Leu Gly Glu Ile Asn Thr Ser Ala Lys Leu
            100                 105                 110

Ser Val Leu Glu Glu Glu Gln Leu Pro Pro Gly Phe Pro Ser Ile Asp
        115                 120                 125

Met Gly Pro Gln Leu Lys Val Val Glu Lys Ala Arg Thr Ala Thr Met
    130                 135                 140

Leu Cys Ala Ala Gly Gly Asn Pro Asp Pro Glu Ile Ser Trp Phe Lys
145                 150                 155                 160

```
Asp Phe Leu Pro Val Asp Pro Ala Thr Ser Asn Gly Arg Ile Lys Gln
                165                 170                 175

Leu Arg Ser Gly Ala Leu Gln Ile Glu Ser Ser Glu Glu Ser Asp Gln
            180                 185                 190

Gly Lys Tyr Glu Cys Val Ala Thr Asn Ser Ala Gly Thr Arg Tyr Ser
        195                 200                 205

Ala Pro Ala Asn Leu Tyr Val Arg Val Arg Arg Val Ala Pro Arg Phe
    210                 215                 220

Ser Ile Pro Pro Ser Ser Gln Glu Val Met Pro Gly Ser Val Asn
225                 230                 235                 240

Leu Thr Cys Val Ala Val Gly Ala Pro Met Pro Tyr Val Lys Trp Met
                245                 250                 255

Met Gly Ala Glu Glu Leu Thr Lys Glu Asp Glu Met Pro Val Gly Arg
            260                 265                 270

Asn Val Leu Glu Leu Ser Asn Val Val Arg Ser Ala Asn Tyr Thr Cys
        275                 280                 285

Val Ala Ile Ser Ser Leu Gly Met Ile Glu Ala Thr Ala Gln Val Thr
    290                 295                 300

Val Lys Ala Leu Pro Lys Pro Ile Asp Leu Val Thr Glu Thr
305                 310                 315                 320

Thr Ala Thr Ser Val Thr Leu Thr Trp Asp Ser Gly Asn Ser Glu Pro
                325                 330                 335

Val Thr Tyr Tyr Gly Ile Gln Tyr Arg Ala Ala Gly Thr Glu Gly Pro
            340                 345                 350

Phe Gln Glu Val Asp Gly Val Ala Thr Thr Arg Tyr Ser Ile Gly Gly
        355                 360                 365

Leu Ser Pro Phe Ser Glu Tyr Ala Phe Arg Val Leu Ala Val Asn Ser
    370                 375                 380

Ile Gly Arg Gly Pro Pro Ser Glu Ala Val Arg Ala Arg Thr Gly Glu
385                 390                 395                 400

Gln Ala Pro Ser Ser Pro Pro Arg Arg Val Gln Ala Arg Met Leu Ser
                405                 410                 415

Ala Ser Thr Met Leu Val Gln Trp Glu Pro Pro Glu Glu Pro Asn Gly
            420                 425                 430

Leu Val Arg Gly Tyr Arg Val Tyr Tyr Thr Pro Asp Ser Arg Arg Pro
        435                 440                 445

Pro Asn Ala Trp His Lys His Asn Thr Asp Ala Gly Leu Leu Thr Thr
    450                 455                 460

Val Gly Ser Leu Leu Pro Gly Ile Thr Tyr Ser Leu Arg Val Leu Ala
465                 470                 475                 480

Phe Thr Ala Val Gly Asp Gly Pro Pro Ser Pro Thr Ile Gln Val Lys
                485                 490                 495

Thr Gln Gln Gly Val Pro Ala Gln Pro Ala Asp Phe Gln Ala Glu Val
            500                 505                 510

Glu Ser Asp Thr Arg Ile Gln Leu Ser Trp Leu Leu Pro Pro Gln Glu
        515                 520                 525

Arg Ile Ile Met Tyr Glu Leu Val Tyr Trp Ala Ala Glu Asp Glu Asp
    530                 535                 540

Gln Gln His Lys Val Thr Phe Asp Pro Thr Ser Ser Tyr Thr Leu Glu
545                 550                 555                 560

Asp Leu Lys Pro Asp Thr Leu Tyr Arg Phe Gln Leu Ala Ala Arg Ser
                565                 570                 575

Asp Met Gly Val Gly Val Phe Thr Pro Thr Ile Glu Ala Arg Thr Ala
            580                 585                 590
```

```
Gln Ser Thr Pro Ser Ala Pro Pro Gln Lys Val Met Cys Val Ser Met
            595                 600                 605

Gly Ser Thr Thr Val Arg Val Ser Trp Val Pro Pro Ala Asp Ser
            610                 615                 620

Arg Asn Gly Val Ile Thr Gln Tyr Ser Val Ala His Glu Ala Val Asp
625                 630                 635                 640

Gly Glu Asp Arg Gly Arg His Val Val Asp Gly Ile Ser Arg Glu His
                645                 650                 655

Ser Ser Trp Asp Leu Val Gly Leu Glu Lys Trp Thr Glu Tyr Arg Val
            660                 665                 670

Trp Val Arg Ala His Thr Asp Val Gly Pro Gly Pro Glu Ser Ser Pro
            675                 680                 685

Val Leu Val Arg Thr Asp Glu Asp Val Pro Ser Gly Pro Pro Arg Lys
            690                 695                 700

Val Glu Val Glu Pro Leu Asn Ser Thr Ala Val His Val Tyr Trp Lys
705                 710                 715                 720

Leu Pro Val Pro Ser Lys Gln His Gly Gln Ile Arg Gly Tyr Gln Val
                725                 730                 735

Thr Tyr Val Arg Leu Glu Asn Gly Glu Pro Arg Gly Leu Pro Ile Ile
            740                 745                 750

Gln Asp Val Met Leu Ala Glu Ala Gln Trp Arg Pro Glu Glu Ser Glu
            755                 760                 765

Asp Tyr Glu Thr Thr Ile Ser Gly Leu Thr Pro Glu Thr Thr Tyr Ser
            770                 775                 780

Val Thr Val Ala Ala Tyr Thr Thr Lys Gly Asp Gly Ala Arg Ser Lys
785                 790                 795                 800

Pro Lys Ile Val Thr Thr Thr Gly Ala Val Pro Gly Arg Pro Thr Met
                805                 810                 815

Met Ile Ser Thr Thr Ala Met Asn Thr Ala Leu Leu Gln Trp His Pro
            820                 825                 830

Pro Lys Glu Leu Pro Gly Glu Leu Leu Gly Tyr Arg Leu Gln Tyr Cys
            835                 840                 845

Arg Ala Asp Glu Ala Arg Pro Asn Thr Ile Asp Phe Gly Lys Asp Asp
            850                 855                 860

Gln His Phe Thr Val Thr Gly Leu His Lys Gly Thr Thr Tyr Ile Phe
865                 870                 875                 880

Arg Leu Ala Ala Lys Asn Arg Ala Gly Leu Gly Glu Glu Phe Glu Lys
                885                 890                 895

Glu Ile Arg Thr Pro Glu Asp Leu Pro Ser Gly Phe Pro Gln Asn Leu
            900                 905                 910

His Val Thr Gly Leu Thr Thr Ser Thr Thr Glu Leu Ala Trp Asp Pro
            915                 920                 925

Pro Val Leu Ala Glu Arg Asn Gly Arg Ile Ile Ser Tyr Thr Val Val
            930                 935                 940

Phe Arg Asp Ile Asn Ser Gln Gln Glu Leu Gln Asn Ile Thr Asp Thr
945                 950                 955                 960

Thr Arg Phe Thr Leu Thr Gly Leu Lys Pro Asp Thr Thr Tyr Asp Ile
                965                 970                 975

Lys Val Arg Ala Trp Thr Ser Lys Gly Ser Gly Pro Leu Ser Pro Ser
            980                 985                 990

Ile Gln Ser Arg Thr Met Pro Val Glu Gln Val Phe Ala Lys Asn Phe
            995                 1000                1005

Arg Val Ala Ala Ala Met Lys Thr Ser Val Leu Leu Ser Trp Glu
```

-continued

```
                   1010               1015                1020

Val Pro Asp Ser Tyr Lys Ser Ala Val Pro Phe Lys Ile Leu Tyr
1025                1030                1035

Asn Gly Gln Ser Val Glu Val Asp Gly His Ser Met Arg Lys Leu
1040                1045                1050

Ile Ala Asp Leu Gln Pro Asn Thr Glu Tyr Ser Phe Val Leu Met
1055                1060                1065

Asn Arg Gly Ser Ser Ala Gly Gly Leu Gln His Leu Val Ser Ile
1070                1075                1080

Arg Thr Ala Pro Asp Leu Leu Pro His Lys Pro Leu Pro Ala Ser
1085                1090                1095

Ala Tyr Ile Glu Asp Gly Arg Phe Asp Leu Ser Met Pro His Val
1100                1105                1110

Gln Asp Pro Ser Leu Val Arg Trp Phe Tyr Ile Val Val Val Pro
1115                1120                1125

Ile Asp Arg Val Gly Gly Ser Met Leu Thr Pro Arg Trp Ser Thr
1130                1135                1140

Pro Glu Glu Leu Glu Leu Asp Glu Leu Leu Glu Ala Ile Glu Gln
1145                1150                1155

Gly Gly Glu Glu Gln Arg Arg Arg Arg Arg Gln Ala Glu Arg Leu
1160                1165                1170

Lys Pro Tyr Val Ala Ala Gln Leu Asp Val Leu Pro Glu Thr Phe
1175                1180                1185

Thr Leu Gly Asp Lys Lys Asn Tyr Arg Gly Phe Tyr Asn Arg Pro
1190                1195                1200

Leu Ser Pro Asp Leu Ser Tyr Gln Cys Phe Val Leu Ala Ser Leu
1205                1210                1215

Lys Glu Pro Met Asp Gln Lys Arg Tyr Ala Ser Ser Pro Tyr Ser
1220                1225                1230

Asp Glu Ile Val Val Gln Val Thr Pro Ala Gln Gln Gln Glu Glu
1235                1240                1245

Pro Glu Met Leu Trp Val Thr Gly Pro Val Leu Ala Val Ile Leu
1250                1255                1260

Ile Ile Leu Ile Val Ile Ala Ile Leu Leu Phe Lys Arg Lys Arg
1265                1270                1275

Thr His Ser Pro Ser Ser Lys Asp Glu Gln Ser Ile Gly Leu Lys
1280                1285                1290

Asp Ser Leu Leu Ala His Ser Ser Asp Pro Val Glu Met Arg Arg
1295                1300                1305

Leu Asn Tyr Gln Thr Pro Gly Met Arg Asp His Pro Pro Ile Pro
1310                1315                1320

Ile Thr Asp Leu Ala Asp Asn Ile Glu Arg Leu Lys Ala Asn Asp
1325                1330                1335

Gly Leu Lys Phe Ser Gln Glu Tyr Glu Ser Ile Asp Pro Gly Gln
1340                1345                1350

Gln Phe Thr Trp Glu Asn Ser Asn Leu Glu Val Asn Lys Pro Lys
1355                1360                1365

Asn Arg Tyr Ala Asn Val Ile Ala Tyr Asp His Ser Arg Val Ile
1370                1375                1380

Leu Thr Ser Ile Asp Gly Val Pro Gly Ser Asp Tyr Ile Asn Ala
1385                1390                1395

Asn Tyr Ile Asp Gly Tyr Arg Lys Gln Asn Ala Tyr Ile Ala Thr
1400                1405                1410
```

```
Gln Gly Pro Leu Pro Glu Thr Met Gly Asp Phe Trp Arg Met Val
1415                1420                1425

Trp Glu Gln Arg Thr Ala Thr Val Val Met Met Thr Arg Leu Glu
1430                1435                1440

Glu Lys Ser Arg Val Lys Cys Asp Gln Tyr Trp Pro Ala Arg Gly
1445                1450                1455

Thr Glu Thr Cys Gly Leu Ile Gln Val Thr Leu Leu Asp Thr Val
1460                1465                1470

Glu Leu Ala Thr Tyr Thr Val Arg Thr Phe Ala Leu His Lys Ser
1475                1480                1485

Gly Ser Ser Glu Lys Arg Glu Leu Arg Gln Phe Gln Phe Met Ala
1490                1495                1500

Trp Pro Asp His Gly Val Pro Glu Tyr Pro Thr Pro Ile Leu Ala
1505                1510                1515

Phe Leu Arg Arg Val Lys Ala Cys Asn Pro Leu Asp Ala Gly Pro
1520                1525                1530

Met Val Val His Cys Ser Ala Gly Val Gly Arg Thr Gly Cys Phe
1535                1540                1545

Ile Val Ile Asp Ala Met Leu Glu Arg Met Lys His Glu Lys Thr
1550                1555                1560

Val Asp Ile Tyr Gly His Val Thr Cys Met Arg Ser Gln Arg Asn
1565                1570                1575

Tyr Met Val Gln Thr Glu Asp Gln Tyr Val Phe Ile His Glu Ala
1580                1585                1590

Leu Leu Glu Ala Ala Thr Cys Gly His Thr Glu Val Pro Ala Arg
1595                1600                1605

Asn Leu Tyr Ala His Ile Gln Lys Leu Gly Gln Val Pro Pro Gly
1610                1615                1620

Glu Ser Val Thr Ala Met Glu Leu Glu Phe Lys Leu Leu Ala Ser
1625                1630                1635

Ser Lys Ala His Thr Ser Arg Phe Ile Ser Ala Asn Leu Pro Cys
1640                1645                1650

Asn Lys Phe Lys Asn Arg Leu Val Asn Ile Met Pro Tyr Glu Leu
1655                1660                1665

Thr Arg Val Cys Leu Gln Pro Ile Arg Gly Val Glu Gly Ser Asp
1670                1675                1680

Tyr Ile Asn Ala Ser Phe Leu Asp Gly Tyr Arg Gln Gln Lys Ala
1685                1690                1695

Tyr Ile Ala Thr Gln Gly Pro Leu Ala Glu Ser Thr Glu Asp Phe
1700                1705                1710

Trp Arg Met Leu Trp Glu His Asn Ser Thr Ile Ile Val Met Leu
1715                1720                1725

Thr Lys Leu Arg Glu Met Gly Arg Glu Lys Cys His Gln Tyr Trp
1730                1735                1740

Pro Ala Glu Arg Ser Ala Arg Tyr Gln Tyr Phe Val Val Asp Pro
1745                1750                1755

Met Ala Glu Tyr Asn Met Pro Gln Tyr Ile Leu Arg Glu Phe Lys
1760                1765                1770

Val Thr Asp Ala Arg Asp Gly Gln Ser Arg Thr Ile Arg Gln Phe
1775                1780                1785

Gln Phe Thr Asp Trp Pro Glu Gln Gly Val Pro Lys Thr Gly Glu
1790                1795                1800

Gly Phe Ile Asp Phe Ile Gly Gln Val His Lys Thr Lys Glu Gln
1805                1810                1815
```

```
Phe Gly Gln Asp Gly Pro Ile Thr Val His Cys Ser Ala Gly Val
    1820                1825                1830

Gly Arg Thr Gly Val Phe Ile Thr Leu Ser Ile Val Leu Glu Arg
    1835                1840                1845

Met Arg Tyr Glu Gly Val Val Asp Met Phe Gln Thr Val Lys Thr
    1850                1855                1860

Leu Arg Thr Gln Arg Pro Ala Met Val Gln Thr Glu Asp Gln Tyr
    1865                1870                1875

Gln Leu Cys Tyr Arg Ala Ala Leu Glu Tyr Leu Gly Ser Phe Asp
    1880                1885                1890

His Tyr Ala Thr
    1895

<210> SEQ ID NO 41
<211> LENGTH: 9
<212> TYPE: PRT
<213> ORGANISM: Artificial sequence
<220> FEATURE:
<223> OTHER INFORMATION: Peptide

<400> SEQUENCE: 41

Met Ser Trp Leu Phe Gly Ile Asn Lys
1               5

<210> SEQ ID NO 42
<211> LENGTH: 7
<212> TYPE: PRT
<213> ORGANISM: Artificial sequence
<220> FEATURE:
<223> OTHER INFORMATION: Peptide

<400> SEQUENCE: 42

Thr Leu Ser Glu Glu Thr Arg
1               5

<210> SEQ ID NO 43
<211> LENGTH: 19
<212> TYPE: PRT
<213> ORGANISM: Artificial sequence
<220> FEATURE:
<223> OTHER INFORMATION: Peptide

<400> SEQUENCE: 43

Gln Thr Val Leu Glu Ser Ile Arg Thr Ala Gly Thr Leu Phe Gly Glu
1               5                   10                  15

Gly Phe Arg

<210> SEQ ID NO 44
<211> LENGTH: 8
<212> TYPE: PRT
<213> ORGANISM: Artificial sequence
<220> FEATURE:
<223> OTHER INFORMATION: Peptide

<400> SEQUENCE: 44

Leu Gly Lys Pro Ser Leu Val Arg
1               5

<210> SEQ ID NO 45
<211> LENGTH: 11
<212> TYPE: PRT
<213> ORGANISM: Artificial sequence
<220> FEATURE:
<223> OTHER INFORMATION: Peptide
```

```
<400> SEQUENCE: 45

Trp Ser Asn Phe Asp Pro Thr Gly Leu Glu Arg
1               5                   10

<210> SEQ ID NO 46
<211> LENGTH: 8
<212> TYPE: PRT
<213> ORGANISM: Artificial sequence
<220> FEATURE:
<223> OTHER INFORMATION: Peptide

<400> SEQUENCE: 46

Ile Thr Val Leu Glu Ala Leu Arg
1               5

<210> SEQ ID NO 47
<211> LENGTH: 14
<212> TYPE: PRT
<213> ORGANISM: Artificial sequence
<220> FEATURE:
<223> OTHER INFORMATION: Peptide

<400> SEQUENCE: 47

Cys Ser Glu Val Ala Arg Leu Thr Glu Gly Met Ser Gly Arg
1               5                   10

<210> SEQ ID NO 48
<211> LENGTH: 9
<212> TYPE: PRT
<213> ORGANISM: Artificial sequence
<220> FEATURE:
<223> OTHER INFORMATION: Peptide

<400> SEQUENCE: 48

Ala Ala Arg Glu Leu Glu His Ser Arg
1               5

<210> SEQ ID NO 49
<211> LENGTH: 8
<212> TYPE: PRT
<213> ORGANISM: Artificial sequence
<220> FEATURE:
<223> OTHER INFORMATION: Peptide

<400> SEQUENCE: 49

Gln Arg Tyr Glu Asp Gln Leu Lys
1               5

<210> SEQ ID NO 50
<211> LENGTH: 7
<212> TYPE: PRT
<213> ORGANISM: Artificial sequence
<220> FEATURE:
<223> OTHER INFORMATION: Peptide

<400> SEQUENCE: 50

Asp Ile Ala Ile Ala Thr Arg
1               5

<210> SEQ ID NO 51
<211> LENGTH: 9
<212> TYPE: PRT
<213> ORGANISM: Artificial sequence
<220> FEATURE:
<223> OTHER INFORMATION: Peptide

<400> SEQUENCE: 51
```

```
Ala Thr Leu Asn Ala Phe Leu Tyr Arg
1               5
```

<210> SEQ ID NO 52
<211> LENGTH: 15
<212> TYPE: PRT
<213> ORGANISM: Artificial sequence
<220> FEATURE:
<223> OTHER INFORMATION: Peptide

<400> SEQUENCE: 52

```
Met Tyr Phe Asp Lys Tyr Val Leu Lys Pro Ala Thr Glu Gly Lys
1               5                   10                  15
```

<210> SEQ ID NO 53
<211> LENGTH: 8
<212> TYPE: PRT
<213> ORGANISM: Artificial sequence
<220> FEATURE:
<223> OTHER INFORMATION: Peptide

<400> SEQUENCE: 53

```
Leu Ala Gln Phe Asp Tyr Gly Arg
1               5
```

<210> SEQ ID NO 54
<211> LENGTH: 22
<212> TYPE: PRT
<213> ORGANISM: Artificial sequence
<220> FEATURE:
<223> OTHER INFORMATION: Peptide

<400> SEQUENCE: 54

```
Val Gln Asp Ala Val Gln Gln His Gln Gln Lys Met Cys Trp Leu Lys
1               5                   10                  15

Ala Glu Gly Pro Gly Arg
            20
```

<210> SEQ ID NO 55
<211> LENGTH: 9
<212> TYPE: PRT
<213> ORGANISM: Artificial sequence
<220> FEATURE:
<223> OTHER INFORMATION: Peptide

<400> SEQUENCE: 55

```
Gly Leu Gly Asp Arg Pro Ala Pro Lys
1               5
```

<210> SEQ ID NO 56
<211> LENGTH: 10
<212> TYPE: PRT
<213> ORGANISM: Artificial sequence
<220> FEATURE:
<223> OTHER INFORMATION: Peptide

<400> SEQUENCE: 56

```
Ala Thr Val Glu Arg Glu Met Glu Leu Arg
1               5                   10
```

<210> SEQ ID NO 57
<211> LENGTH: 10
<212> TYPE: PRT
<213> ORGANISM: Artificial sequence
<220> FEATURE:
<223> OTHER INFORMATION: Peptide

<400> SEQUENCE: 57

Ala Glu Arg Glu Asn Ala Asp Ile Ile Arg
1               5                   10

<210> SEQ ID NO 58
<211> LENGTH: 8
<212> TYPE: PRT
<213> ORGANISM: Artificial sequence
<220> FEATURE:
<223> OTHER INFORMATION: Peptide

<400> SEQUENCE: 58

Asn Ala Thr Leu Val Ala Gly Arg
1               5

<210> SEQ ID NO 59
<211> LENGTH: 12
<212> TYPE: PRT
<213> ORGANISM: Artificial sequence
<220> FEATURE:
<223> OTHER INFORMATION: Peptide

<400> SEQUENCE: 59

Asn Ile Leu Met Tyr Gly Pro Pro Gly Thr Gly Lys
1               5                   10

<210> SEQ ID NO 60
<211> LENGTH: 23
<212> TYPE: PRT
<213> ORGANISM: Artificial sequence
<220> FEATURE:
<223> OTHER INFORMATION: Peptide

<400> SEQUENCE: 60

Gly Glu Gly Ala Gly Pro Pro Pro Leu Pro Ala Gln Pro Gly
1               5                   10                  15

Ala Glu Gly Gly Gly Asp Arg
            20

<210> SEQ ID NO 61
<211> LENGTH: 11
<212> TYPE: PRT
<213> ORGANISM: Artificial sequence
<220> FEATURE:
<223> OTHER INFORMATION: Peptide

<400> SEQUENCE: 61

Gln Gln Gln Leu Leu Asn Glu Glu Asn Leu Arg
1               5                   10

<210> SEQ ID NO 62
<211> LENGTH: 18
<212> TYPE: DNA
<213> ORGANISM: Artificial sequence
<220> FEATURE:
<223> OTHER INFORMATION: Forward primer

<400> SEQUENCE: 62
gtgcgagcat gtcgtggc                                              18

<210> SEQ ID NO 63
<211> LENGTH: 19
<212> TYPE: DNA
<213> ORGANISM: Artificial sequence
<220> FEATURE:
<223> OTHER INFORMATION: Reverse primer

```
<400> SEQUENCE: 63
ggagatccac agctcacgg                                              19

<210> SEQ ID NO 64
<211> LENGTH: 68
<212> TYPE: DNA
<213> ORGANISM: Artificial sequence
<220> FEATURE:
<223> OTHER INFORMATION: Forward primer

<400> SEQUENCE: 64
cgggatccag catggaacaa aaacttattt ctgaagaaga tctgtcgtgg ctcttcggca    60
ttaacaag                                                            68

<210> SEQ ID NO 65
<211> LENGTH: 27
<212> TYPE: DNA
<213> ORGANISM: Artificial sequence
<220> FEATURE:
<223> OTHER INFORMATION: Reverse primer

<400> SEQUENCE: 65
cggaattcga ctcaggatgg ggaaggc                                       27

<210> SEQ ID NO 66
<211> LENGTH: 25
<212> TYPE: DNA
<213> ORGANISM: Artificial sequence
<220> FEATURE:
<223> OTHER INFORMATION: Forward primer

<400> SEQUENCE: 66
cgggatcctg cgagcatgtc gtggc                                         25

<210> SEQ ID NO 67
<211> LENGTH: 24
<212> TYPE: DNA
<213> ORGANISM: Artificial sequence
<220> FEATURE:
<223> OTHER INFORMATION: Reverse primer

<400> SEQUENCE: 67
gctctagagg atggggaagg ctcg                                          24
```

BINDING MOLECULES FOR TREATMENT AND DETECTION OF CANCER

CROSS-REFERENCE TO RELATED APPLICATIONS

This application is a continuation of U.S. patent application Ser. No. 11/665,102, filed Apr. 10, 2007, now U.S. Pat. No. 7,858,086 (Dec. 28, 2010), which is a national phase entry under 35 U.S.C. §371 of International Patent Application PCT/EP2005/055163, filed Oct. 11, 2005, published in English as International Patent Publication WO 2006/040322 A1 on Apr. 20, 2006, which claims the benefit under Article 8 of the Patent Cooperation Treaty to European Patent Application Serial No. 04104999.0, filed Oct. 12, 2004, and to U.S. Provisional Patent Application Ser. No. 60/618,332, filed Oct. 12, 2004, the entire disclosure of each of which is hereby incorporated herein by this reference.

TECHNICAL FIELD

The invention relates to the field of medicine. The invention in particular relates to binding molecules capable of specifically binding to cancer-associated antigens. The binding molecules are useful in the prevention, treatment and detection of cancer.

BACKGROUND DESCRIBED HEREIN

Cancer describes a class of diseases characterized by the uncontrolled growth of aberrant cells. It is the second leading cause of human death next to coronary disease. Worldwide, millions of people die from cancer every year. In the United States alone, cancer causes the death of well over a half million people each year, with some 1.4 million new cases diagnosed per year.

One form of cancer, accounting for about 3% of all cancers in the United States of America, is leukemia. This malignant disease is characterized by an abnormal proliferation of white blood cells which can be detected in the peripheral blood and/or bone marrow. Leukemia can be broadly classified into acute and chronic leukemia. Acute leukemia can be subclassified into myeloid and lymphoid leukemia in a variety of ways, including cell morphology and cytochemistry.

Acute myeloid leukemia (AML) is the most common form of leukemia accounting for about 50% of all leukemia cases and even 85% of all acute leukemia cases involving adults.

The standard treatment regime for AML is chemotherapy, which often includes an anthracycline. This results in a 70% complete remission (CR) rate in AML patients. Anthracycline therapy, however, is associated with severe side effects, including myelosuppression and dose-limiting cardiotoxicity, as well as a significant incidence of relapse. Less than 20% of CR patients survive in the long term. Relapsed AML disease exhibits multiple drug resistance (MDR), making the relapsed disease frequently refractory to further treatment with a variety of chemotherapeutic agents, including drugs.

In the light thereof, therapies for AML have been developed. Some therapies make use of antibodies capable of binding to AML-associated antigens such as CD33 or CD45 (see, WO 2004/043344). Although AML-associated antigens have been described, there is still a great need for new AML antigens useful in antibody and other biological therapies. In addition, there is a corresponding need for AML-associated antigens which may be useful as markers for antibody-based diagnostic and imaging methods, hopefully leading to the development of earlier diagnosis and greater prognostic precision.

SUMMARY DESCRIBED HEREIN

Described are new tumor target antigens for antibody-based prophylaxis and associated therapies. In particular, antigens associated with AML are provided. Furthermore, several binding molecules capable of binding to the tumor-associated antigens have been identified and obtained by using phage display technology. Furthermore, methods of producing these binding molecules and the use of the binding molecules in diagnosis, prevention and treatment of neoplastic disorders and diseases, in particular AML, have been described.

DETAILED DESCRIPTION

Figure 1:
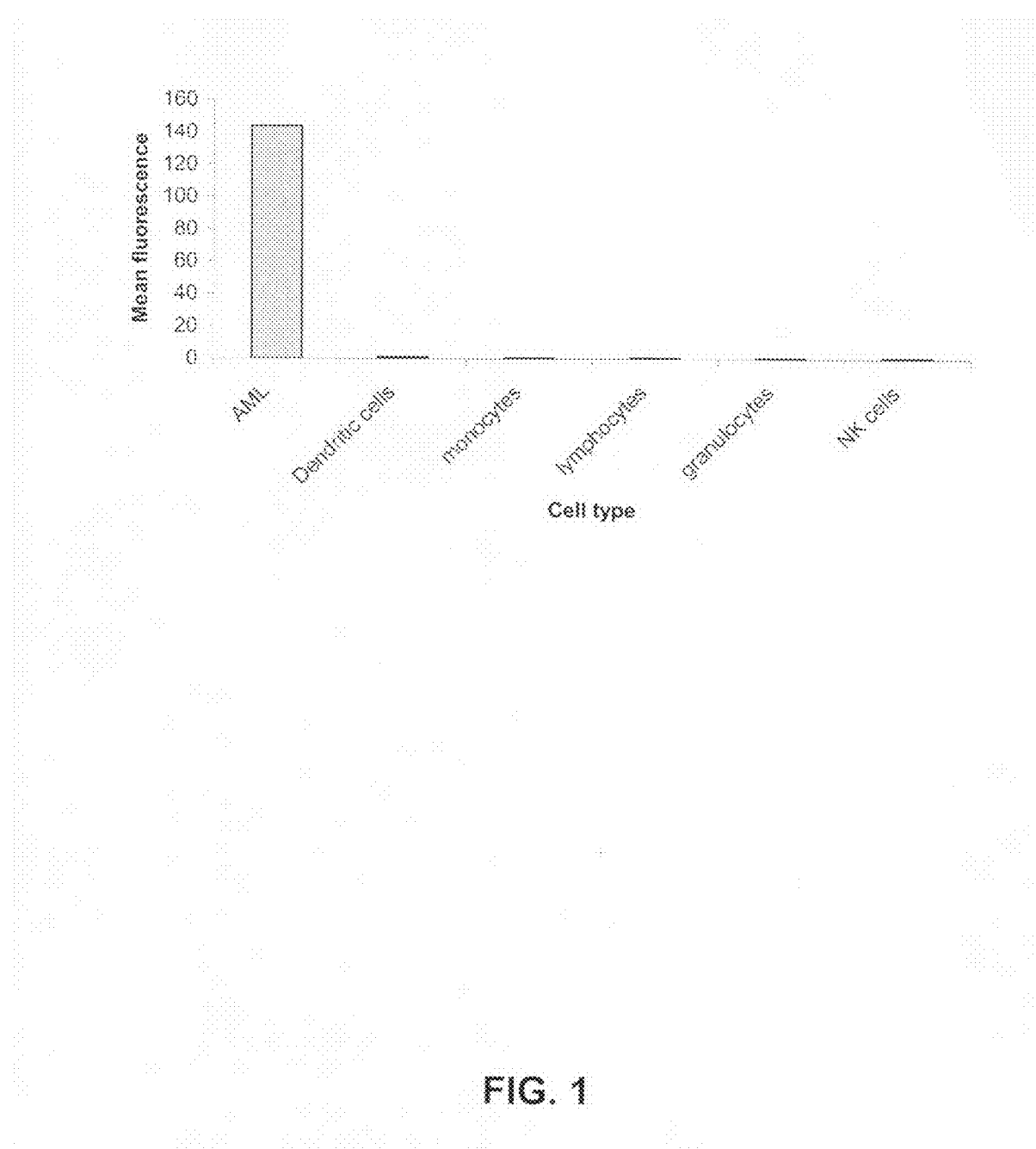
FIG. 1 shows the binding intensity (depicted in mean fluorescence) of the phage antibody SC02-401 to AML in relation to the binding intensity of the phage antibody to different cell populations in peripheral blood of a healthy donor.

Encompassed are binding molecules capable of binding to an antigen present on tumor cells, such as AML cells. As used herein the term "acute myeloid leukemia (AML)" is characterized by an uncontrolled proliferation of progenitor cells of myeloid origin including, but not limited to, myeloid progenitor cells, myelomonocytic progenitor cells, and immature megakaryoblasts. Subtypes of AML according to the FAB classification include FAB-M0, FAB-M1, FAB-M2, FAB-M3, FAB-M4, FAB-M5, FAB-M6 and FAB-M7.

The described binding molecules may be human binding molecules. They can be intact immunoglobulin molecules, such as polyclonal or monoclonal antibodies, such as chimeric, humanized or in particular human monoclonal antibodies, or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, diabodies, triabodies, tetrabodies, and (poly)peptides that contain at least a fragment of an immunoglobulin that is sufficient to confer specific antigen binding to the (poly)peptides. The term "binding molecule," as used herein also includes the immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG 1, IgG2, IgG3 and IgG4. The methods of production of antibodies are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference.

The binding molecules can be used in non-isolated or isolated form. Furthermore, the binding molecules can be used alone or in a mixture comprising at least one binding molecule (or variant or fragment thereof). In other words, the binding molecules can be used in combination, e.g., as a pharmaceutical composition comprising two or more binding molecules or fragments thereof. For example, binding molecules having different, but complementary, activities can be combined in a single therapy to achieve a desired therapeutic or diagnostic effect, but alternatively, binding molecules having identical activities can also be combined in a single therapy to achieve a desired therapeutic or diagnostic effect. The mixture may further comprise at least one other therapeutic agent. Typically, the binding molecules can bind to their binding partners, i.e., the AML-associated antigens described herein, with an affinity constant (Kd-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can be measured using surface plasmon resonance, i.e., an optical phenomenon that allows for the analysis of real-time biospecific interactions by detection of alterations in protein concentrations within a biosensor matrix, for example, using the BIAcore system (Pharmacia Biosensor AB, Uppsala, Sweden).

The binding molecules may bind to the AML-associated antigens described herein in soluble form or may bind to the AML-associated antigens described herein bound or attached to a carrier or substrate, e.g., microtiter plates, membranes and beads, etc. Carriers or substrates may be made of glass, plastic (e.g., polystyrene), polysaccharides, nylon, nitrocellulose, or TEFLON®, etc. The surface of such supports may be solid or porous and of any convenient shape. Furthermore, the binding molecules may bind to the AML-associated antigens in purified or non-purified form and/or in isolated or non-isolated form. Preferably, the binding molecules are capable of binding to the antigens when they are associated with cells, such as a human cells positive for the antigen, e.g., AML cells or cells transfected with the AML-associated antigens described herein, or portions or parts of these cells comprising the AML-associated antigens or a fragment thereof such as the extracellular part of the antigens. As the AML-associated antigens according to the invention are overexpressed by tumor cells as compared to normal cells of the same tissue type, the binding molecules according to the invention can be used to selectively target the tumor cells. In particular, the AML-associated antigens according to the invention are overexpressed by AML cells as compared to normal blood cells.

The binding molecules described herein, which stay bound to the surface upon binding to the antigens present on the surface of target cells, such as AML cells, may be used in the format of naked binding molecules to support possible effector functions of antibody-dependent cellular cytotoxicity (ADCC) and/or complement-dependent cytotoxicity (CDC). Assays to distinguish ADCC or CDC are well known to the person skilled in the art. The described naked antibodies may also induce apoptosis of target cells in another way than by means of ADCC or CDC. Alternatively, they may internalize upon binding to the AML-associated antigens described herein. Internalization of binding molecules can be assayed by techniques known to the person skilled in the art.

In certain embodiments, the binding molecules comprise at least a CDR3 region, preferably a heavy chain CDR3 region, comprising the amino acid sequence of SEQ ID NO:1 or SEQ ID NO:2.

In another embodiment, the binding molecules comprise a heavy chain variable region comprising the amino acid sequence of SEQ ID NO:3 or SEQ ID NO:4.

In yet a further embodiment, the binding molecules comprise a heavy chain variable region comprising the amino acid sequence shown in SEQ ID NO:3 and a light chain variable region comprising the amino acid sequence of SEQ ID NO:7, or a heavy chain variable region comprising the amino acid sequence shown in SEQ ID NO:4 and a light chain variable region comprising the amino acid sequence of SEQ ID NO:8.

Another aspect described herein includes functional variants of binding molecules or fragments thereof as defined herein. Molecules are considered to be functional variants of a binding molecule according to the invention, if the variants are capable of competing for specifically binding to the AML-associated antigens described herein with the parent binding molecules. In other words, when the functional variants are still capable of binding to the AML-associated antigens or a portion thereof. Functional variants include, but are not limited to, derivatives that are substantially similar in primary structural sequence, but which contain e.g., in vitro or in vivo modifications, chemical and/or biochemical, that are not found in the parent binding molecule. Such modifications are well known to the skilled artisan.

Alternatively, functional variants can be binding molecules comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxy termini. Functional variants according to the invention may have the same or different, either higher or lower, binding affinities compared to the parent binding molecule but are still capable of binding to the AML-associated antigens described herein. For instance, functional variants according to the invention may have increased or decreased binding affinities for the AML-associated antigens described herein compared to the parent binding molecules. Preferably, the amino acid sequences of the variable regions, including, but not limited to, framework regions, hypervariable regions, in particular the CDR3 regions, are modified. Functional variants intended to fall within the scope described herein have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular, at least about 97% to about 99% amino acid sequence homology with the parent binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parent binding molecules or parts thereof by general molecular biology methods known in the art including, but not limited to, error prone PCR, oligonucleotide-directed mutagenesis and site-directed mutagenesis.

In an embodiment the AML-associated antigen is leukocyte antigen-related receptor protein tyrosine phosphatase (LAR PTP). LAR PTP is a prototype of a family of transmembrane phosphatases whose extracellular domains are composed of three Ig and several fibronectin type III domains (Streuli et al. 1988). LAR PTP is expressed in cells of many different lineages including epithelial cells, smooth muscle cells and cardiac myocytes and increased levels of LAR PTP expression and differential patterns of extracellular alternative splicing were found in breast cancer cell lines and pheochromocytoma tumor tissue.

Another aspect described herein pertains to a human binding molecule as herein defined capable of specifically binding to LAR PTP or the extracellular part thereof. The amino acid sequence of LAR PTP is shown in SEQ ID NO:40. The extracellular part of the protein consists of amino acids 1-1259 (Streuli et al., 1992). In certain embodiments, the human binding molecule specifically binding to LAR PTP comprises at least a heavy chain CDR3 region comprising the amino acid sequence of SEQ ID NO:1. The binding molecule capable of specifically binding to LAR PTP can be used in indications wherein LAR PTP has been suggested to play a role such as inter alia obesity, Type II diabetes, and tumors. As LAR PTP is overexpressed in AML cells the binding molecule capable of specifically binding to LAR PTP can be used as a medicament, in detection, prevention and/or treatment of AML. The binding molecules described herein have specific immunoreactivity with AML subtypes M0, M1/2 and M3 and can thus advantageously be used as a medicament, in detection, prevention and/or treatment of these specific AML subtypes.

In another embodiment, the AML-associated antigen is a polypeptide comprising the amino acid sequence of SEQ ID NO:6. This protein has been called ATAD3A. It contains a potential ATP-ase region from amino acids 347-467 and potentially belongs to the AAA-superfamily of ATP-ases. In general, ATP-ases are associated with a wide variety of cellular activities, including membrane fusion, proteolysis, and DNA replication. The invention further provides that the polypeptide is overexpressed in tumors, particularly in AML. The polypeptide is expressed by all AML subtypes.

An aspect described herein is concerned with a nucleic acid molecule encoding the polypeptide comprising the amino acid sequence of SEQ ID NO:6. In a specific embodiment the nucleic acid molecule comprises the nucleotide sequence of SEQ ID NO:5.

Another aspect described herein is concerned with a pharmaceutical composition comprising a polypeptide comprising the amino acid sequence of SEQ ID NO:6 or a nucleic acid molecule encoding the polypeptide. The pharmaceutical composition further comprises a pharmaceutically acceptable carrier. Such a composition could be used as a vaccine.

In yet another embodiment, provided is a binding molecule as herein defined capable of specifically binding to a polypeptide comprising the amino acid sequence of SEQ ID NO:6. The polypeptide comprising the amino acid sequence of SEQ ID NO:6, a pharmaceutical composition comprising this polypeptide or nucleic acid molecule encoding this polypeptide or binding molecule specifically binding to this polypeptide can be used as a medicament for inter alia the detection, prevention and/or treatment of cancer, in particular for the detection, prevention and/or treatment of AML.

Naturally occurring truncated or secreted forms, naturally occurring variant forms (e.g., alternatively spliced forms) and naturally occurring allelic variants of the AML-associated antigens described herein are also a part described herein. Binding molecules described herein may also be capable of specifically binding to non-naturally occurring variants or analogues of these antigens as long as the modifications do not abolish the binding of the binding molecules to the antigens.

A nucleic acid molecule encoding the polypeptide as described above, preferably comprising the amino acid sequence of SEQ ID NO:6, preferably comprises the nucleotide sequence as shown in SEQ ID NO:5. The nucleic acid molecule may be used as a vaccine or for making a vaccine.

In yet a further aspect, described are immunoconjugates, i.e., molecules comprising at least one binding molecule as described above and further comprising at least one tag, such as a therapeutic moiety that inhibits or prevents the function of cells and/or causes destruction of cells. Also contemplated are mixtures of immunoconjugates or mixtures of at least one immunoconjugates and another molecule, such as a therapeutic or diagnostic agent or another binding molecule or immunoconjugate. In a further embodiment, the immunoconjugates described herein may comprise more than one tag. These tags can be the same or distinct from each other and can be joined/conjugated non-covalently to the binding molecules. The tags can also be joined/conjugated directly to the binding molecules through covalent bonding. Alternatively, the tags can be joined/conjugated to the binding molecules by means of one or more linking compounds. Techniques for conjugating tags to binding molecules, are well known, see, e.g., Arnon et al., "Monoclonal Antibodies For Immunotargeting Of Drugs In Cancer Therapy," p. 243-256 in *Monoclonal Antibodies And Cancer Therapy* (1985), edited by Reisfeld et al., A. R. Liss, Inc.; Hellstrom et al., "Antibodies For Drug Delivery," p. 623-653 in *Controlled Drug Delivery*, 2nd edition (1987), edited by Robinson et al., Marcel Dekker, Inc.; Thorpe, "Antibody Carriers Of Cytotoxic Agents," p. 475-506 in *Cancer Therapy: A Review, in Monoclonal Antibodies '84: Biological And Clinical Applications* (1985), edited by Pinchera et al.; "Analysis, Results, and Future Prospective of the Therapeutic Use of Radiolabeled Antibody in Cancer Therapy," p. 303-316 in *Monoclonal Antibodies For Cancer Detection And Therapy* (1985), edited by Baldwin et al., Academic Press.

Tags include, but are not limited to, toxic substances, radioactive substances, liposomes, enzymes, polynucleotide sequences, plasmids, proteins, peptides or combinations thereof. Toxic substances include, but are not limited to, cytotoxic agents, such as small molecule toxins or chemotherapeutic agents, or enzymatically active toxins of bacterial, fungal, plant or animal origin, or fragments thereof. In general, suitable chemotherapeutic agents are described in *Remington's Pharmaceutical Sciences*, 18th edition (1990), edited by A. R. Gennaro, Mack Publishing Co., Philadelphia; and in Goodman and Gilman's *The Pharmacological Basis of Therapeutics*, 7th edition (1985), edited by A. G. Gilman, L. S. Goodman, T. W. Rall and F. Murad, MacMillan Publishing Co., New York. Suitable chemotherapeutic agents that are still in the experimental phase are known to those of skill in the art and might also be used as toxic substances in the invention.

Fusion proteins comprising enzymatically active toxins and binding molecules of the immunoconjugate described herein can be produced by methods known in the art such as, e.g., recombinantly by constructing nucleic acid molecules comprising nucleotide sequences encoding the binding molecules in frame with nucleotide sequences encoding the enzymatically active toxin and then expressing the nucleic acid molecules. Alternatively, fusion proteins can be produced chemically by conjugating, directly or indirectly via for instance a linker, binding molecules as defined herein to enzymatically active toxins. Immunoconjugates comprising enzymes may be useful in antibody-directed enzyme-prodrug therapy (ADEPT).

Also contemplated are binding molecules of the immunoconjugate described herein that are labeled with radionuclides. The skilled person knows suitable radionuclides. The choice of radionuclide will be dependent on many factors such as, e.g., the type of disease to be treated, the stage of the disease to be treated, the patient to be treated and the like. Binding molecules can be attached to radionuclides directly or indirectly via a chelating agent by methods well known in the art.

In another embodiment, the binding molecules of the immunoconjugate described herein can be conjugated to liposomes to produce so called immunoliposomes. A liposome may be conjugated to one or more binding molecules, the binding molecules being either the same or different. A variety of methods are available for preparing liposomes. These methods are well known in the art and include, but are not limited to, sonication, extrusion, high pressure/homogenization, microfluidization, detergent dialysis, calcium induced fusion of small liposome vesicles, and ether infusion methods. The liposomes may be multilamellar vesicles, but preferably the liposomes are unilamellar vesicles such as small unilamellar (200-500 Å) or large unilamellar vesicles (500-5000 Å). The drugs that can be loaded into liposomes include, but are not limited to, the toxic substances mentioned above. Liposomes having loaded different drugs and different liposomes, each liposome having loaded one kind of drug, may be alternative embodiments of liposomes that can be used and these embodiments are therefore also contemplated in the invention. Binding molecules described herein may be attached at the surface of the liposomes or to the terminus of polymers such as polyethylene glycol that are grafted at the surface of the liposomes using conventional chemical coupling techniques.

In yet another embodiment, the binding molecules described herein may be linked to water-soluble, biodegradable polymers, such as for instance polymers of hydroxypropylmethacrylamine (HPMA).

In another aspect, the binding molecules described herein may be conjugated/attached to one or more antigens. These antigens may be antigens that are recognized by the immune system of a subject to whom the binding molecule-antigen conjugate is administered. The antigens may be identical, but may also be different. Conjugation methods for attaching the antigens and binding molecules are well known in the art and include, but are not limited to, the use of cross-linking agents.

Alternatively, the binding molecules as described herein can be conjugated to tags and be used for detection and/or analytical and/or diagnostic purposes. The tags used to label the binding molecules for those purposes depend on the specific detection/analysis/diagnosis techniques and/or methods used such as inter alia immunohistochemical staining of tissue samples, flow cytometric detection, scanning laser cytometric detection, fluorescent immunoassays, enzyme-linked immunosorbent assays (ELISAs), radioimmunoassays (RIAs), bioassays (e.g., growth inhibition assays), Western blotting applications, etc. The binding molecules described herein may also be conjugated to photoactive agents or dyes such as fluorescent and other chromogens or dyes to use the so obtained immunoconjugates in photoradiation, phototherapy, or photodynamic therapy.

When the immunoconjugates described herein are used for in vivo diagnostic use, the binding molecules can also be made detectable by conjugation to, e.g., magnetic resonance imaging (MRI) contrast agents, ultrasound contrast agents or to X-ray contrast agents, or by radioisotopic labeling.

Furthermore, the binding molecules or immunoconjugates described herein can also be attached to solid supports, which are particularly useful for immunoassays or purification of the binding partner. Such solid supports might be porous or nonporous, planar or nonplanar. The binding molecules can also, for example, usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of cells that express or display the AML-associated antigens or fragments thereof. As another example, the binding molecules described herein can usefully be attached to the surface of a microtiter plate for ELISA. It is clear to the skilled artisan that any of the tags described above can also be conjugated to the new antigens described herein.

Another aspect described herein concerns nucleic acid molecules as defined herein encoding binding molecules described herein. In yet another aspect, provided are nucleic acid molecules encoding at least the binding molecules specifically binding to the AML-associated antigens described above. In certain embodiments, the nucleic acid molecules are isolated or purified.

The skilled person will appreciate that functional variants of the nucleic acid molecules described herein are also intended to be a part described herein. Functional variants are nucleic acid sequences that can be directly translated, using the standard genetic code, to provide an amino acid sequence identical to that translated from the parent nucleic acid molecules. Preferably, the nucleic acid molecules encode binding molecules comprising a CDR3 region, preferably a heavy chain CDR3 region, comprising the amino acid sequence of SEQ ID NO:1 or SEQ ID NO:2. Even more preferably, the nucleic acid molecules encode binding molecules comprising a heavy chain variable region comprising the amino acid sequence of SEQ ID NO:3 or SEQ ID NO:4. In yet another embodiment, the nucleic acid molecules encode binding molecules comprising a heavy chain variable region comprising the amino acid sequence of SEQ ID NO:3 and a light chain variable region comprising the amino acid sequence of SEQ ID NO:7, or they encode a heavy chain variable region comprising the amino acid sequence of SEQ ID NO:4 and a light chain variable region comprising the amino acid sequence of SEQ ID NO:8. In a specific embodiment, the nucleic acid molecules encoding the binding molecules described herein comprise the nucleotide sequence of SEQ ID NO:9 or SEQ ID NO:10.

It is another aspect to provide vectors, e.g., nucleic acid constructs, comprising one or more nucleic acid molecules according to the invention. Vectors can be derived from plasmids; cosmids; phages; plant viruses; or animal viruses. Vectors can be used for cloning and/or for expression of the binding molecules described herein and might even be used for gene therapy purposes. Vectors comprising one or more nucleic acid molecules according to the invention operably linked to one or more expression regulating nucleic acid molecules are also covered by the invention. The choice of vector is dependent on the recombinant procedures followed and the host used. Introduction of vectors in host cells can be effected by inter alia calcium phosphate transfection, virus infection, DEAE-dextran mediated transfection, lipofectamine transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. Vectors comprising one or more nucleic acid molecules encoding the binding molecules as described above operably linked to one or more nucleic acid molecules encoding proteins or peptides that can be used to isolate the binding molecules are also covered by the invention.

Hosts containing one or more copies of the vectors mentioned hereinabove are an additional subject described herein. Preferably, the hosts are host cells. Host cells include, but are not limited to, cells of mammalian, plant, insect, fungal or bacterial origin. Bacterial cells include, but are not limited to, cells from Gram positive bacteria such as several species of the genera *Bacillus, Streptomyces* and *Staphylococcus* or cells of Gram negative bacteria such as several species of the genera *Escherichia* and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells. Transformed (transgenic) plants or plant cells are produced by known methods. Expression systems using mammalian cells such as Chinese Hamster Ovary (CHO) cells, COS cells, BHK cells or Bowes melanoma cells are preferred in the invention. Mammalian cells provide expressed proteins with posttranslational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are human retina cells and immortalized with nucleic acids comprising adenoviral E1 sequences such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B. V.). For the purposes of this application "PER.C6" refers to cells deposited under number 96022940 or ancestors, passages up-stream or downstream as well as descendants from ancestors of deposited cells, as well as derivatives of any of the foregoing.

Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

It is another aspect to provide a method of producing binding molecules or functional variants thereof, preferably human binding molecules or functional variants thereof. The method comprises the steps of a) culturing a host as described above under conditions conducive to the expression of the binding molecules, and b) optionally, recovering the expressed binding molecules. The expressed binding molecules can be recovered from the cell free extract, but preferably they are recovered from the culture medium. Methods to recover proteins, such as binding molecules, from cell free extracts or culture medium are well known to the man skilled in the art. Binding molecules as obtainable by the above described method are also a part described herein.

Alternatively, next to the expression in hosts, such as host cells, the binding molecules described herein can be produced synthetically by conventional peptide synthesizers or in cell free translation systems using RNAs derived from DNA molecules according to the invention. Binding molecule as obtainable by the above described synthetic production methods or cell free translation systems are also a part described herein. In addition, the above-mentioned methods of producing binding molecules can also be used to produce the AML-associated antigens described herein.

In yet another alternative embodiment, binding molecules according to the invention may be generated by transgenic non-human mammals. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, N.Y.; and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference.

In a further aspect, provided is a method of identifying binding molecules, preferably human binding molecules such as human monoclonal antibodies or fragments thereof, or nucleic acid molecules and comprises the steps of a) contacting a phage library of binding molecules, preferably human binding molecules, with material comprising the AML-associated antigens described herein or fragments thereof, b) selecting at least once for a phage binding to the material comprising the AML-associated antigens described herein or fragments thereof, and c) separating and recovering the phage binding to the material comprising the AML-associated antigens described herein or fragments thereof. The selection step according to the invention is preferably performed in the presence of at least part of the AML-associated antigens described herein, e.g., cells transfected with expression plasmids of the AML-associated antigens, isolated AML-associated antigens, the extracellular part thereof, fusion proteins comprising such, and the like. In an embodiment the selection step is performed in the presence of AML cells. Prior to or concurrent with this selection step the phage library of binding molecules can be contacted to normal blood cells and/or tumor cell lines expressing the AML-associated antigens described herein. Phage display methods for identifying and obtaining binding molecules, e.g., antibodies, are by now well-established methods known by the person skilled in the art. They are, e.g., described in U.S. Pat. No. 5,696,108; Burton and Barbas, 1994; and de Kruif et al., 1995b. For the construction of phage display libraries, collections of human monoclonal antibody heavy and light chain variable region genes are expressed on the surface of bacteriophage, preferably filamentous bacteriophage, particles in, for example, single chain Fv (scFv) or in Fab format (see, de Kruif et al., 1995b). Large libraries of antibody fragment-expressing phages typically contain more than $1.0*10^9$ antibody specificities and may be assembled from the immunoglobulin V regions expressed in the B-lymphocytes of immunized- or non-immunized individuals. Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Antigen-specific phage antibodies can be selected from the library by immobilizing target antigens on a solid phase and subsequently exposing the target antigens to a phage library to allow binding of phages expressing antibody fragments specific for the solid phase-bound antigen. Non-bound phages are removed by washing and bound phages eluted from the solid phase for infection of *Escherichia coli* (*E. coli*) bacteria and subsequent propagation. Multiple rounds of selection and propagation are usually required to sufficiently enrich for phages binding specifically to the target antigen. Phages may also be selected for binding to complex antigens such as complex mixtures of proteins or whole cells such as cells transfected with antigen expression plasmids or cells naturally expressing the AML-associated antigens described herein. Selection of antibodies on whole cells has the advantage that target antigens are presented in their native configuration, i.e., unperturbed by possible conformational changes that might have been introduced in the case where an antigen is immobilized to a solid phase. Antigen-specific phage antibodies can be selected from the library by incubating a cell population of interest, expressing known and unknown antigens on their surface, with the phage antibody library to let, for example, the scFv or Fab part of the phage bind to the antigens on the cell surface. After incubation and several washes to remove unbound and loosely attached phages, the cells of interest are stained with specific fluorescent labeled antibodies and separated on a Fluorescent Activated Cell Sorter (FACS). Phages that have bound with their scFv or Fab part to these cells are eluted and used to infect *E. coli* to allow amplification of the new specificity. Generally, one or more selection rounds are required to separate the phages of interest from the large excess of non-binding phages. Monoclonal phage preparations can be analyzed for their specific staining patterns and allowing identification of the antigen being recognized (De Kruif et al., 1995a). The phage display method can be extended and improved by subtracting non-relevant binders during screening by addition of an excess of non-target molecules that are similar, but not identical, to the target, and thereby strongly enhance the chance of finding relevant binding molecules (This process is referred to as the MABSTRACT® process. MABSTRACT® is a registered trademark of Crucell Holland B.V., see also U.S. Pat. No. 6,265,150, which is incorporated herein by reference).

In yet a further aspect, provided is a method of obtaining a binding molecule or a nucleic acid molecule according to the invention, wherein the method comprises the steps of a) performing the above described method of identifying binding molecules, preferably human binding molecules such as human monoclonal antibodies or fragments thereof according to the invention, or nucleic acid molecules according to the invention, and b) isolating from the recovered phage the human binding molecule and/or the nucleic acid encoding the human binding molecule. Once a new monoclonal phage antibody has been established or identified with the above mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see, Huls et al., 1999; Boel et al., 2000).

In a further aspect, provided are compositions comprising at least one binding molecule, at least one functional variant or fragment thereof, at least one immunoconjugate according to the invention or a combination thereof. In another aspect, provided are compositions comprising the new AML-associated antigens described herein. In addition to that, the compositions may comprise inter alia stabilizing molecules, such as albumin or polyethylene glycol, or salts. If necessary, the binding molecules or antigens described herein may be coated in or on a material to protect them from the action of acids or other natural or non-natural conditions that may inactivate the binding molecules.

In yet a further aspect, provided are compositions comprising at least one nucleic acid molecule as defined in the invention. The compositions may comprise aqueous solutions such as aqueous solutions containing salts (e.g., NaCl or salts as described above), detergents (e.g., SDS) and/or other suitable components.

Furthermore, the invention pertains to pharmaceutical compositions comprising at least one binding molecule according to the invention, at least one functional variant or fragment thereof, at least one immunoconjugate according to the invention, at least one composition according to the invention, or combinations thereof. The invention also provides a pharmaceutical composition comprising the AML-associated antigens described herein. The pharmaceutical composition described herein further comprises at least one pharmaceutically acceptable carrier/excipient. A pharmaceutical composition according to the invention can further comprise at least one other therapeutic, prophylactic and/or diagnostic agent.

Typically, pharmaceutical compositions must be sterile and stable under the conditions of manufacture and storage. The binding molecules, variant or fragments thereof, immunoconjugates, nucleic acid molecules, compositions or antigens described herein can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, variant or fragments thereof, immunoconjugates, nucleic acid molecules or compositions described herein can be in solution and the appropriate pharmaceutically acceptable excipient can be added and/or mixed before or at the time of delivery to provide a unit dosage injectable form. Preferably, the pharmaceutically acceptable excipient used in the invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. The routes of administration can be divided into two main categories, oral and parenteral administration. The preferred administration route is intravenous.

The binding molecules, such as the human binding molecules such as human monoclonal antibodies according to the invention, the variants or fragments thereof, the immunoconjugates according to the invention, the nucleic acid molecules according to the invention, the compositions according to the invention or the pharmaceutical compositions according to the invention can be used as medicaments. They can inter alia be used in the diagnosis, prevention, treatment, or combination thereof, of cancer. The cancer may be AML, however other tumors, such as tumors wherein the new antigens described herein are overexpressed, can also be prevented, treated and/or diagnosed. The binding molecules described herein are suitable for treatment of yet untreated patients suffering from cancer, patients who have been or are treated and are in remission or are not in remission, and patients with a recurrent/refractory cancer. The binding molecules described herein may even be used in the prophylaxis of cancer. In addition, the novel antigens described herein or pharmaceutical compositions comprising such may be used in the diagnosis, prevention, treatment, or combination thereof, of cancer. Preferably, the cancer a tumor wherein the novel antigens are overexpressed such as AML.

The above mentioned molecules or compositions may be employed in conjunction with other molecules useful in diagnosis, prevention and/or treatment. They can be used in vitro, ex vivo or in vivo. The molecules are typically formulated in the compositions and pharmaceutical compositions described herein in a prophylactically, therapeutically or diagnostically effective amount. Dosage regimens can be adjusted to provide the optimum desired response (e.g., a therapeutic response). The molecules and compositions according to the invention are preferably sterile. Methods to render these molecules and compositions sterile are well known in the art. The other molecules useful in diagnosis, prevention and/or treatment can be administered in a similar dosage regimen as proposed for the binding molecules described herein. If the other molecules are administered separately, they may be administered to a subject with cancer prior (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before) to, concomitantly with, or subsequent (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) to the administration of one or more of the binding molecules or pharmaceutical compositions described herein. The dosing regimen is usually sorted out during clinical trials in human patients.

Human binding molecules and pharmaceutical compositions comprising the human binding molecules are particularly useful, and often preferred, when to be administered to human beings as in vivo diagnostic or therapeutic agents, since recipient immune response to the administered antibody will often be substantially less than that occasioned by administration of a monoclonal murine, chimeric or humanized binding molecule.

Alternatively, cells that are genetically engineered to express the binding molecules described herein are administered to patients in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the nucleic acid molecules described herein into the cells. Preferably, the binding molecules are secreted from the cells. The engineered cells which express and preferably secrete the binding molecules as described herein can be introduced into the patient, for example, systemically, e.g., in the circulation, or intraperitoneally. In other embodiments, the cells can be incorporated into a matrix or can be encapsulated and implanted in the body. In a gene therapy setting the binding molecules may be administered in the form of a vector capable of infecting cells of the host, coding for a binding molecule according to the invention.

In another aspect, described is the use of binding molecules, preferably human binding molecules such as human monoclonal antibodies, fragments or variants thereof, immunoconjugates according to the invention, nucleic acid molecules according to the invention, compositions or pharmaceutical compositions according to the invention in the preparation of a medicament for the diagnosis, prophylaxis, treatment, or combination thereof, of cancer such as AML.

Kits comprising at least one binding molecule, preferably human binding molecule such as human monoclonal antibody according to the invention, at least one variant or fragment thereof, at least one immunoconjugate, at least one nucleic acid molecule, at least one composition, at least one pharmaceutical composition, at least one vector, at least one host, or a combination thereof are also a part hereof. Optionally, the above described kits also comprise an AML-associated antigen described herein. Optionally, the above described components of the kits described herein are packed in suitable containers and labeled for diagnosis and/or treatment of the indicated conditions. The above-mentioned components may be stored in unit or multi-dose containers. The kit may further comprise more containers comprising a pharmaceutically acceptable buffer. It may further include other materials desirable from a commercial and user standpoint, including other buffers, diluents, filters, needles, syringes, culture medium for one or more of the suitable hosts. Associated with the kits can be instructions customarily included in commercial packages of therapeutic or diagnostic products, that contain information about, for example, the indications, usage, dosage, manufacture, administration, contraindications and/or warnings concerning the use of such therapeutic or diagnostic products.

Furthermore, described is a method of screening a binding molecule or a functional variant or fragment thereof for specific binding to the same epitope of an AML-associated antigens described herein or fragment thereof, as the epitope bound by the binding molecule according to the invention, wherein the method comprises the steps of (a) contacting a binding molecule (or a functional variant or fragment thereof) to be screened, a binding molecule (or functional fragment or variant thereof) according to the invention and an AML-associated antigen described herein (or a fragment thereof comprising the antigenic determinant), (b) measure if the binding molecule (or functional variant or fragment thereof) to be screened is capable of competing for specifically binding to an AML-associated antigen described herein (or fragment thereof comprising the antigenic determinant) with the binding molecule described herein. Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule described herein, as well as antibodies, antibody fragments and other binding agents that bind to an epitope or binding site sufficiently proximal to an epitope bound by the reference binding molecule for competitive binding between the binding molecules to be screened and the reference binding molecule to occur.

EXAMPLES

To illustrate the invention, the following illustrative examples are provided.

Example 1

Selection of Phages Carrying Single Chain Fv Fragments Specifically Recognizing Human Acute Myeloid Leukemia Cells Antibody fragments were selected using antibody phage display libraries, general phage display technology and MABSTRACT® technology, essentially as described in U.S. Pat. No. 6,265,150 and in WO 98/15833 (both of which are incorporated by reference herein). Furthermore, the methods and helper phages as described in WO 02/103012 (incorporated by reference herein) were used in the invention. For identifying phage antibodies recognizing AML tumor cells phage selection experiments were performed using the erythroid leukemia cell line K562 or the AML cell line called HL60 and primary AML tumor cells that were obtained from bone marrow aspirates of AML patients.

An aliquot of a phage library (500 µl, approximately $10^{13}$ cfu, amplified using CT helper phage (see, WO 02/103012)) was blocked and presubtracted by mixing the library with 10 ml of RPMI 1640 medium with 10% FBS containing $230*10^6$ peripheral blood leukocytes (PBL). The obtained mixture was rotated at 4° C. for 1.5 hours. Hereafter, the cells were pelleted and the supernatant containing the phage library was transferred to a new tube containing a fresh pellet of $230*10^6$ PBL. The cells were resuspended in the phage library supernatant and the mixture was again rotated at 4° C. for 1.5 hours. This procedure was repeated once more and eventually 10 ml of supernatant containing the blocked phage library which was 3 times subtracted with PBL was transferred to a new tube and was kept overnight at 4° C. The next day $4*10^6$ cells of the erythroid leukemia cell line called K562 or AML cell line called HL60 were pelleted in a separate 15 ml tube and the cells were resuspended in 1 ml of RPMI 1640 medium with 10% FBS. To the tube 3.3 ml of the pre-subtracted blocked phage library and 5 ml of RPMI 1640 medium with 10% FBS was added and the mixture was rotated at 4° C. for 2 hours. Hereafter, the obtained mixture was transferred to a 50 ml tube and washed 5 times with 30 ml RPMI 1640 medium with 10% FBS. To the pelleted cells 0.8 ml of 50 mM glycine-HCl pH 2.2 was added, mixed well and left at room temperature for 10 minutes to elute the attached phages. After that, 0.4 ml of 1 M Tris-HCl pH 7.4 was added for neutralization. Then, the cells were pelleted again and the supernatant was used to infect 5 ml of a XL1-Blue *E. coli* culture that had been grown at 37° C. to an OD600 nm of approximately 0.3. The phages were allowed to infect the XL1-Blue bacteria for 30 minutes at 37° C. Subsequently, the mixture was centrifuged for 10 minutes, at 3200*g at room temperature and the bacterial pellet was resuspended in 1 ml 2-trypton yeast extract (2TY) medium. The obtained bacterial suspension was divided over a 2TY agar plate supplemented with tetracycline, ampicillin and glucose. After incubation overnight of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of phosphate buffered saline (PBS) with 1% bovine serum albumin (BSA), filter-sterilized and used for the next round of selection. To this purpose a 500 µl aliquot of the K562-derived amplified sublibrary or HL-60-derived amplified sublibrary was blocked with 2 ml of RPMI 1640 medium with 10% FBS for 30 minutes at 4° C. To the blocked sublibrary $5\times10^6$ thawed primary AML blasts (90% CD33+ CD34+ blasts, FAB type M0) were added that previously had been stained with a PE-labeled anti-CD34 antibody (Becton Dickinson). The obtained mixture rotated at 4° C. for 2.5 hours. Hereafter, the mixture was transferred to a 50 ml tube, washed 3 times with 30 ml cold RPMI 1640 medium with 10% FBS. Subsequently, the mixture was passed over a 70 micron cell strainer and was subjected to flow cytometry. Cell sorting was performed using a FACSVantage flow cytometer (Becton Dickinson). Cells were gated on the basis of low sideward scatter (SSC) combined with CD34-PE staining. Approximately $9*10^5$ cells were sorted. The sorted cells were spun down, the supernatant was saved and the bound phages were eluted from the cells by resuspending the cells in 800 µl 50 mM glycin-HCl pH 2.2 followed by incubation for 5 minutes at room temperature. The obtained mixture was neutralized with 400 µl 1 M Tris-HCl pH 7.4 and added to the rescued supernatant. The eluted phages were used to re-infect XL1-Blue *E. coli* cells as described supra. After the second round of selection, individual *E. coli* colonies were used to prepare monoclonal phage antibodies. Essentially, individual colonies were grown to log-phase in 96 well plate format and infected with CT helper phages after which phage antibody production was allowed to proceed overnight. The produced phage antibodies were PEG/NaCl-precipitated and filter-sterilized and tested using flow cytometry (FACSCalibur, Becton Dickinson) for binding to both the K562 erythroid leukemia cell line or HL-60 acute myeloid leukemia cell line as well as to the primary AML blasts (that were used for the second round selection). Two of the selected phage antibodies, i.e., SC02-361 and SC02-401, bound well to both the primary AML tumor blasts as well as to K562 erythroid leukemia cells or HL-60 cells and were analyzed in further detail (see, examples below).

Example 2

Characterization of scFv SC02-401 and SC02-361

Plasmid DNA was obtained from the selected scFv clones SC02-401 and SC02-361 according to standard techniques known in the art. Thereafter, the nucleotide sequence of scFv clones SC02-401 and SC02-361 was determined according to standard techniques well known to a person skilled in the art. The nucleotide sequence of SC02-401 and SC02-361 are listed in Table 1 and have SEQ ID NO:11 and SEQ ID NO:13, respectively. The amino acid translation of the nucleotide sequences is also listed in Table 1. They have SEQ ID NO:12 and SEQ ID NO:14, respectively. The VH and VL gene identity and amino acid sequence of the heavy chain CDR3 regions are also depicted in Table 1.

Example 3

Expression of the Antigen Recognized by SC02-401 and SC02-361 on Primary AML Samples, Tumor Cell Lines and Normal Hematopoetic Cells The distribution of the target antigens recognized by the phage antibodies SC02-401 and SC02-361 was analyzed by flow cytometry using primary AML samples, tumor cell lines and normal hematopoetic cells derived from peripheral blood. For flow cytometry analysis, phage antibodies were first blocked in an equal volume of PBS containing 4% w/v milk protein (MPBS) for 15 minutes at 4° C. prior to the staining of the various cells. The binding of the phage antibodies to the cells was visualized using a biotinylated anti-M13 antibody (Santa Cruz Biotechnology) followed by addition of streptavidin-allophycocyanin or streptavidin-phycoerythrin (Caltag). In addition to the phage antibody the following antibody combinations were used: CD45-PerCP, indirect labeling of SC02-401 and SC02-361 with myc biotin and streptavidin-PE and CD33-APC. The cells were washed twice with PBS containing 1% w/v BSA and resuspended in binding buffer for annexin V conjugates (Caltag) supplemented with annexin V-FITC for exclusion of dead and apoptotic cells. Cells were analyzed on a FACS caliber (BD) using CellQuest software. For final analysis, blasts cells were gated based on low side scatter versus CD45 expression. A sample was considered positive if more than 20% of the cells expressed the antigen of interest (compared to staining with a control antibody CR2428.

The CD45 positive blast population of a set of different primary AML blasts (inter alia FAB subtypes: FAB-M0, FAB-M1, FAB-M2, FAB-M3, FAB-M4 and FAB-M5) was analyzed for binding of the SC02-401 and SC02-361 phage antibody in a direct comparison with CD33 expression. Phage antibody SC02-401 showed strong binding to FAB-M0, FAB-M1/2 and FAB-M3 and binding to FAB-M5. SC02-401 did not show significant binding to primary AML blasts of the FAB-M1, FAB-M2, FAB-M4, FAB-M5a and FAB-M5b type as compared to a control phage antibody CR 2428 (see, Table 2).

Phage antibody SC02-361 showed strong binding to FAB-M0, FAB-M1, FAB-M1/2, FAB-M2, FAB-M3, FAB-M4, FAB-M5, FAB-M5a and FAB-M5b type as compared to a control phage antibody CR2428 (see, Table 3).

Analysis of a panel of tumor cell lines of both hematopoetic and non-hematopoetic origin revealed that expression of the antigen recognized by SC02-401 was not restricted to a subset of tumor cell lines of myeloid origin (HL-60 and NB4), since it was also expressed by other tumor cell lines, namely U937, K562, 293T, LS 174T and HEp-2 (see, Table 4). The antigen recognized by SC02-361 was detectable on tumor cell lines of myeloid origin and additionally on the tumor cell lines U937, LS 174T and HEp-2.

Flow cytometric analysis was performed by gating the lymphocyte-, monocyte- and granulocyte subpopulations on the basis of their forward- and side-scatter characteristics. The lymphocytes were further divided in B-cells and T-cells by staining the sample with an APC-conjugated anti-CD19 antibody (Pharmingen) and a FITC-conjugated anti-CD3 antibody (Becton Dickinson). Within peripheral blood, subsets of leukocytes were analyzed by staining with antibodies recognizing the cell surface antigens CD14 (FITC-labeled, Becton Dickinson), CD16 (FITC-labeled, Pharmingen) and CD33 (APC-labeled, Becton Dickinson). Within peripheral blood the SC02-401 phage antibody did not significantly bind to any of the subsets analyzed (see, Table 5). SC02-361 did recognize a subpopulation of monocytes and dendritic cells, but did not significantly bind to granulocytes, B- and T-cells, Natural Killer (NK) cells, erythrocytes or platelets (see, Table 5).

Figure 2:
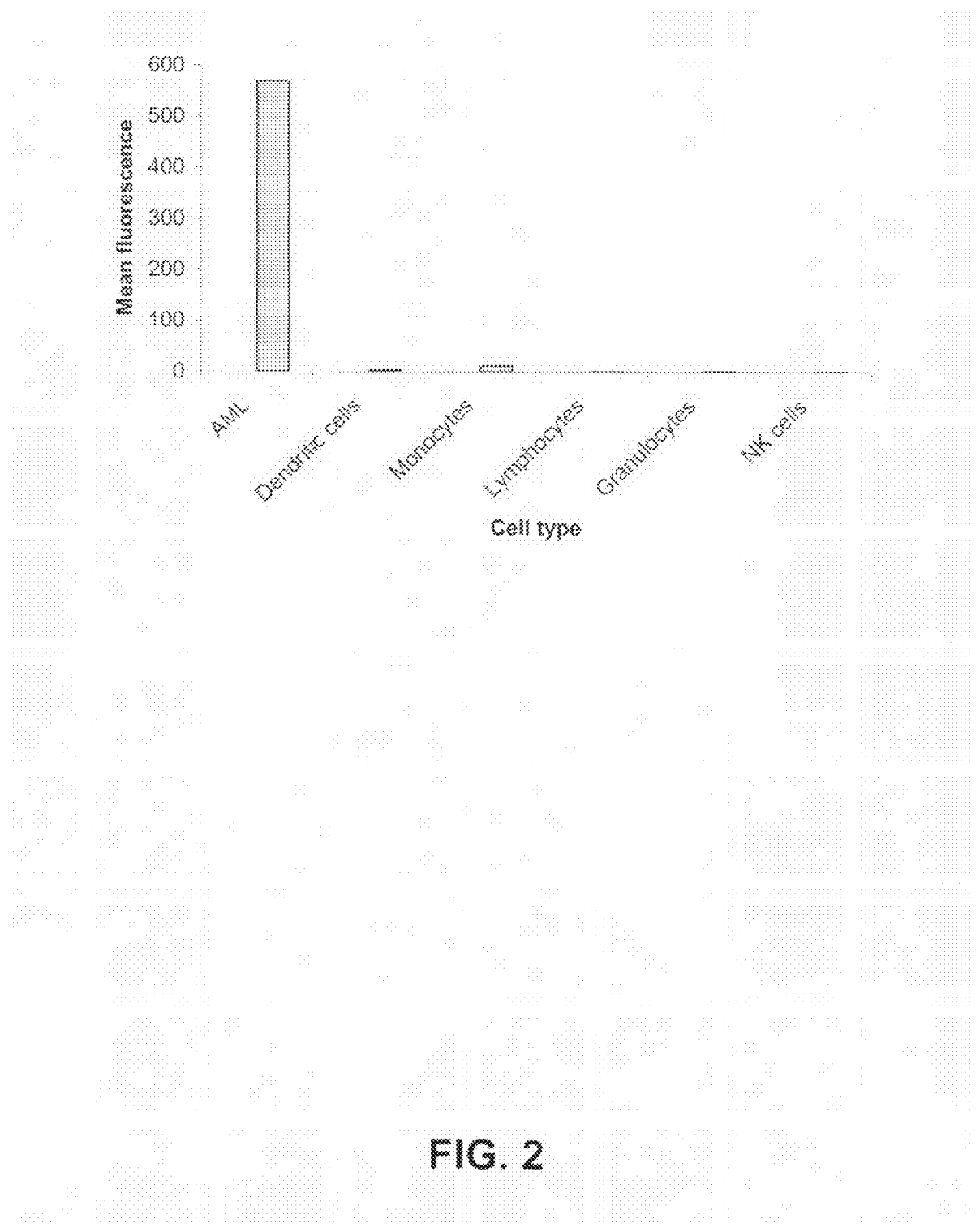
FIG. 2 shows the binding intensity (depicted in mean fluorescence) of the phage antibody SC02-361 to AML in relation to the binding intensity of the phage antibody to different cell populations in peripheral blood of a healthy donor.

In FIGS. 1 and 2 is shown that the binding intensity of the phage antibody SC02-401 and SC02-361, respectively, to AML cells is much higher than the binding intensity of the phage antibody to different cell populations in peripheral blood of a healthy donor indicating overexpression of the antigens recognized by the antibodies in AML. The mean fluorescence of SC02-401 and SC02-361 was calculated for AML and the different cell populations. Furthermore, the mean fluorescence of a control antibody (called SC02-006 and binding to thyroglobulin) was calculated for AML and the different cell populations (data not shown) and this value was deducted from the mean fluorescence value of SC02-401 or SC02-361.

From these combined expression data it was concluded that the antigens recognized by SC02-401 and SC02-361 represent a good target antigen for diagnosis, prevention and/or treatment of cancer, in particular of AML.

Example 4

Generation of CR2401 and CR2361 IG1 Molecules

Heavy- and light chain variable regions of the scFvs SC02-401 and SC02-361 were PCR-amplified using oligonucleotides to append restriction sites and/or sequences for expression in IgG expression vectors. The VL chains were amplified using the oligonucleotides 5K-C (SEQ ID NO:15) and 3K-C (SEQ ID NO:16). The PCR products were cloned into vector pcDNA3.1 and the nucleotide sequences were verified according to standard techniques known to the skilled artisan. VH genes were amplified using oligonucleotides 5H-B (SEQ ID NO:17) and Sy3H-a reversed (SEQ ID NO:18). Thereafter, the PCR products were cloned into vector pSyn-03-HCg1 and nucleotide sequences were verified according to standard techniques known to the skilled person in the art.

| | | |
|---|---|---|
| 5H-B: | acctgtcttgaattctccatggccgaggtgcagctggtggagtctg | (SEQ ID NO: 17) |
| Sy3H-a reversed: | ggggccagggcaccctggtgaccgtctccagcgctagcaccaagggc | (SEQ ID NO: 18) |
| 5K-C: | acctgtctcgagttttccatggctgacatccagatgacccagtctccatcctccc | (SEQ ID NO: 15) |
| 3K-C: | caagggaccaaggtggagatcaaacgtaagtgcactttgcggccgctaaggaaaa | (SEQ ID NO: 16) |

The expression constructs of the heavy and light chains were transiently expressed in 293T cells and supernatants containing IgG1 antibodies were obtained. The nucleotide sequences of the heavy chain of CR2401 is shown in SEQ ID NO:19 and the amino acid sequences is shown in SEQ ID NO:20. The nucleotide sequences of the light chain of CR2401 is shown in SEQ ID NO:23 and the amino acid sequences is shown in SEQ ID NO:24. The nucleotide sequences of the heavy chain of CR2361 is shown in SEQ ID NO:21 and the amino acid sequences is shown in SEQ ID NO:22. The nucleotide sequences of the light chain of CR2361 is shown in SEQ ID NO:25 and the amino acid sequences is shown in SEQ ID NO:26.

The antibodies were purified on protein-A columns and size-exclusion columns using standard purification methods used generally for immunoglobulins (see, for instance WO 00/63403).

Example 5

Immunoprecipitation of Membrane Extractable Antigen Recognized by CR2401 and Membrane Extractable Antigen Recognized by CR2361

To identify whether CR2401 reacted with a membrane extractable antigen, the cell surface of $10^8$ LS174T cells were biotinylated during 1 hour at room temperature with a final concentration of 2 mg sulfo-NHS-LC-LC-biotin in physiological buffer (0.2 M phosphate buffer containing 0.12 M NaCl, pH 7.4). Subsequently, the remaining free biotin was blocked during a 30-minute incubation at room temperature with 10 mM glycine in physiological buffer. After labeling, the cells were washed with cold physiological buffer and solubilized for 30 minutes on ice at a concentration of $3 \times 10^7$ cells/ml in TX-100 lysis buffer (1% Triton X-100, 150 mM NaCl, 50 mM Tris pH 7.4, protease inhibitors (Roche)). The unsoluble material was removed by centrifugation for 30 minutes at 4° C. at 20,000*g. Hereafter, the biotinylated solubilized lysate was pre-cleared with protein-A beads for 2 hours at 4° C. In the mean time, 4 μg of CR2401, control antibody CR2428 (negative control), and control antibody CR2300 IG1 (positive control; antibody directed against CD46, present on every nucleated cell) were coupled to protein-A beads at room temperature. Next, the pre-cleared samples were incubated with the IgGs coupled to the beads for 2 hours at 4° C. The protein-A beads were washed three times for 5 minutes with 1 ml of TX-100 lysis buffer and bound complexes were eluted by the addition of sample loading buffer. The samples were subjected to SDS-PAGE under non-reducing and reducing conditions. After blotting on PVDF membranes, the biotinylated proteins were detected with streptavidin-HRP (Amersham) and enhanced chemiluminescent (Amersham).

Similar steps as above were followed to identify whether CR2361 reacted with a membrane extractable antigen, with the proviso that $10^8$ NB4 cells and a RIPA lysis buffer containing 1% v/v Triton X-100, 0.5% w/v desoxycholate, 0.1% w/v SDS, 150 mM NaCl, 50 mM Tris pH 7.4, protease inhibitors (Roche) were used for immunoprecipitation purposes.

Figure 3:
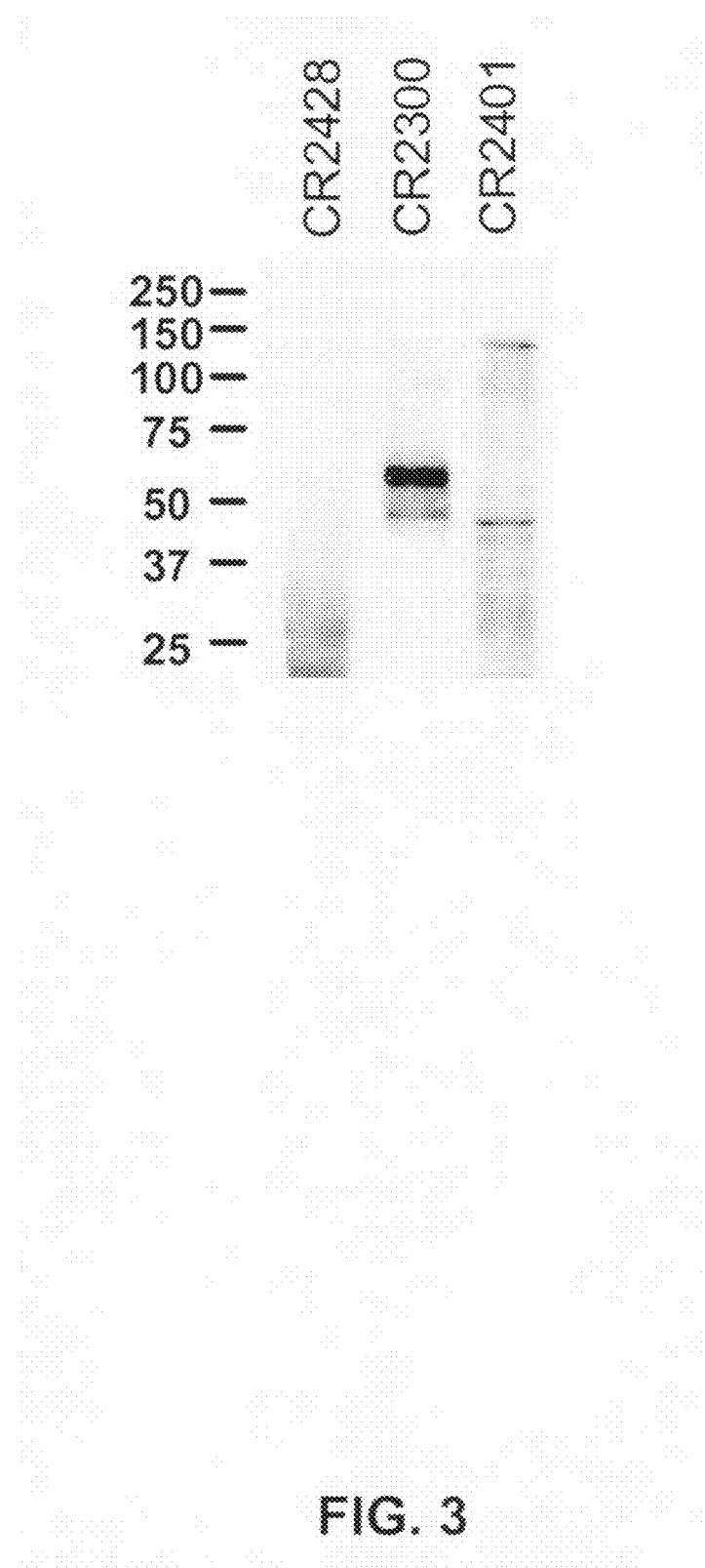
FIG. 3 shows an immunoblot of a LS174T cell lysate immunoprecipitated with a negative control IgG1 (CR2428; left lane), a positive control IgG1 directed against CD46 (CR2300; middle lane), or IgG1 CR2401 (right lane). On the left side of the blot molecular weight markers are indicated.

In the CR2401 immunoprecipitation of the LS174T cell lysate a major band at approximately 150 kDa and one minor band at approximately 45 kDa was detected. None of these bands were present in immunoprecipitations performed with the negative control IgG1 CR2428 or the positive control IgG1 CR2300 directed against CD46 (see, FIG. 3). To establish wash and elution conditions for the big scale purification of immune complexes of CR2401, immunoprecipitates were subjected to washes with different concentrations of NaCl 150 mM-500 mM, and immune complexes were eluted off the protein-A beads using low (pH 2.7) or high (pH 11) pH buffers. The immune complexes were still present after washes with 500 mM NaCl, whereas they became eluted at pH 11 (data not shown).

Figure 4:
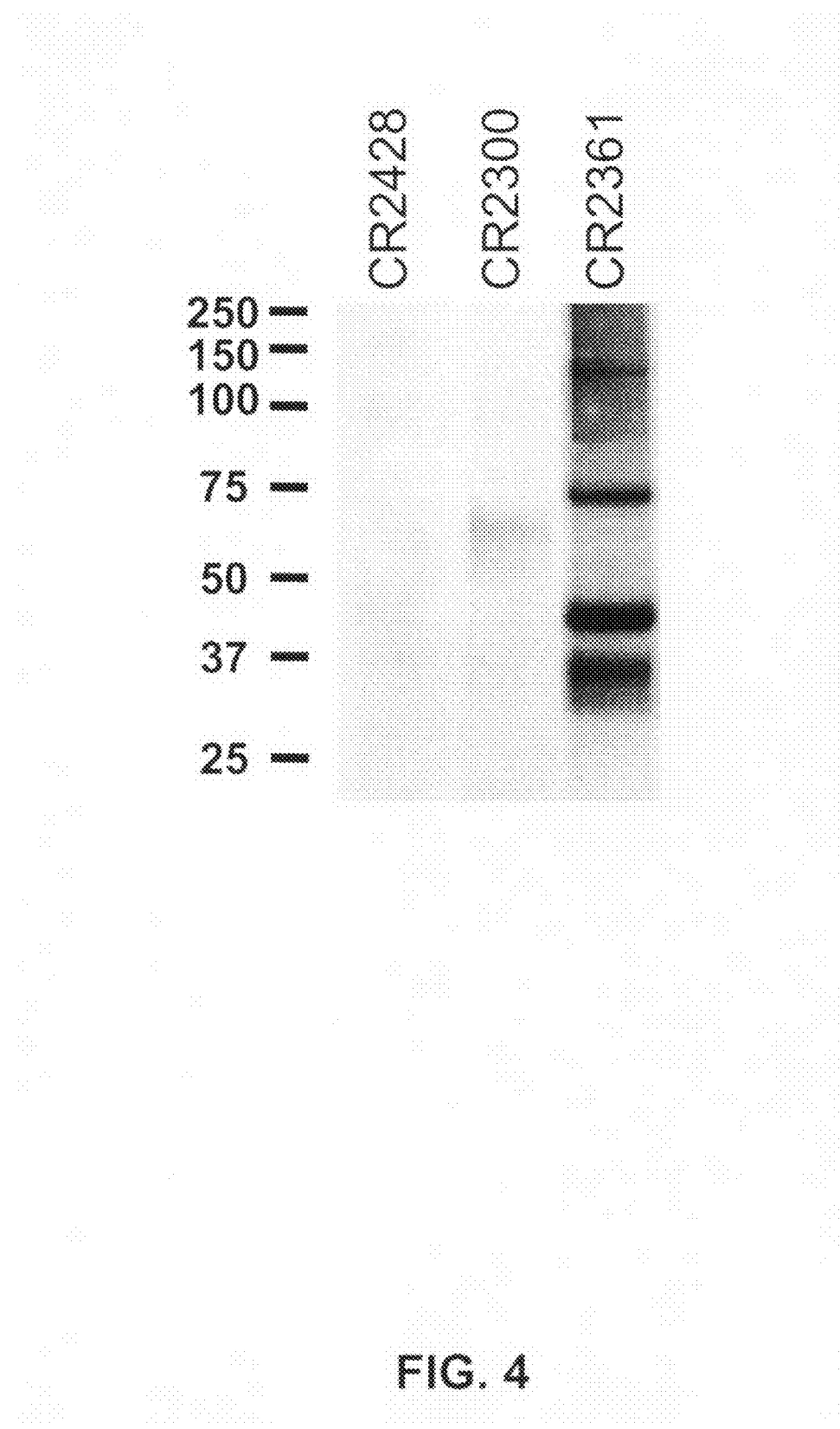
FIG. 4 shows an immunoblot of a NB4 cell lysate immunoprecipitated with a negative control IgG1 (CR2428; left lane), a positive control IgG1 directed against CD46 (CR2300; middle lane), or IgG1 CR2361 (right lane). On the left side of the blot molecular weight markers are indicated.

In the CR2361 immunoprecipitation of the NB4 cell lysate four clear distinct bands running at approximately 30, 40, 75 and 150 kDa were detected. None of these bands were present in immunoprecipitations performed with the negative control IgG1 CR2428 or the positive control IgG CR2300 directed against CD46 (see, FIG. 4). To establish wash and elution conditions for the big scale purification of immune complexes of CR2361, immunoprecipitates were subjected to washes with different concentrations of NaCl 150 mM-500 mM, and immune complexes were eluted off the protein-A beads using low (pH 2.7) or high (pH 11) pH buffers. The immune complexes were still present after washed with 500 mM NaCl, whereas they became eluted at pH 2.7 (data not shown).

Example 6

Purification of the Immune Complexes Reacting with Cr2401 or Cr2361

For the purification of the target antigens of CR2401 and CR2361 affinity columns were prepared by coupling 1.5 mg CR2401 or CR2361 to 1 ml CNBr activated Sepharose-4B beads according to standard techniques known to the skilled artisan. In advance the IgG1s were passed over a 100 kDa ultracentrifugal device to remove incomplete small IgG fragments.

Figure 5:
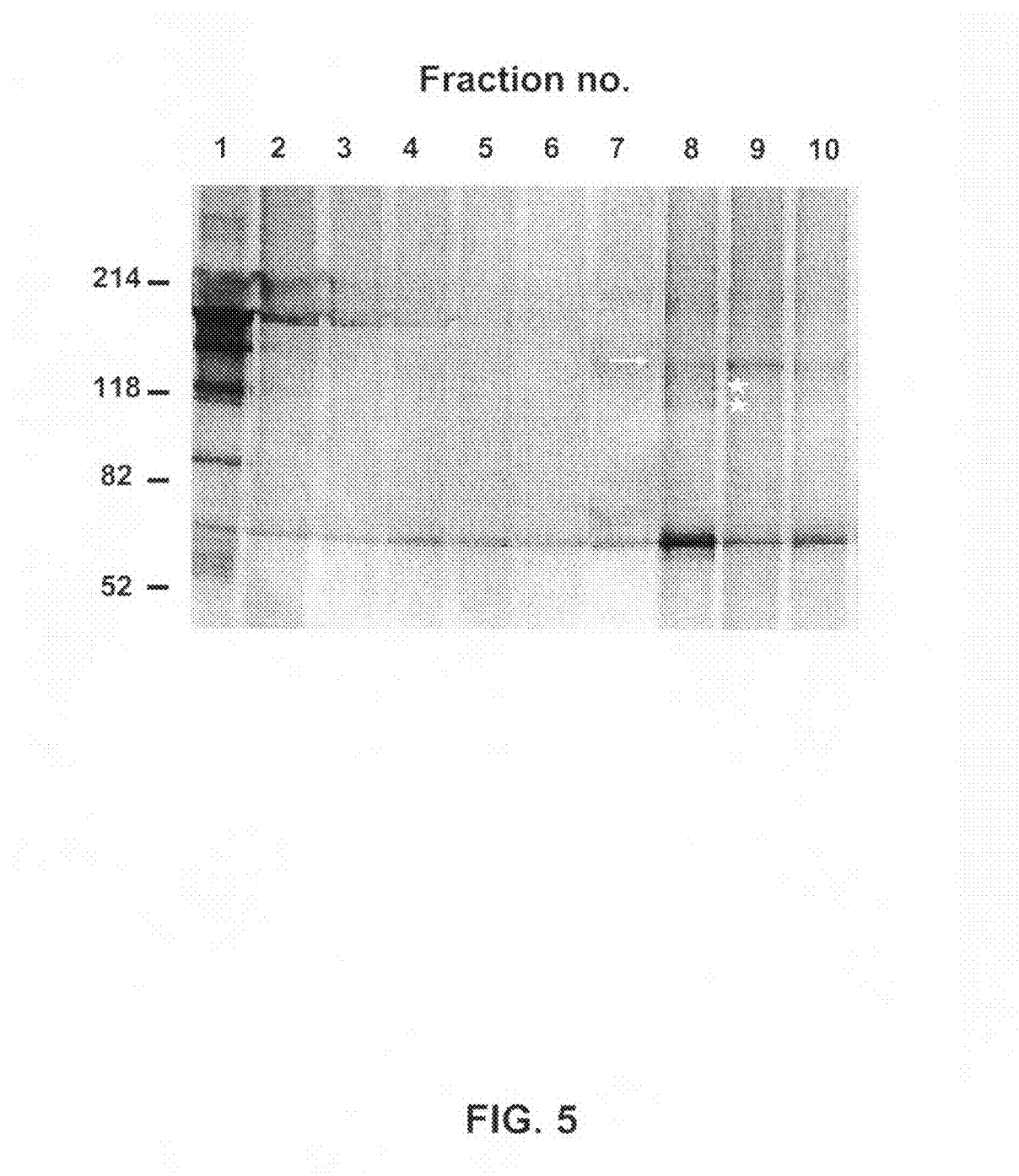
FIG. 5 shows a silver stained SDS-PAGE gel of the proteins eluting from an affinity column of CR2401. The arrow indicates the protein of interest (150 kDa) specifically released from the column in fraction 8-10. The asterisk indicates two protein bands somewhat smaller than 150 kDa. On the left side of the blot molecular weight markers are indicated.

A cell lysate of $5*10^9$ LS174T cells was prepared in TX-100 lysis buffer according to the method described in Example 5. Next, the cell lysate was passed through a 0.22 μm filter to remove aggregates. The cell lysate was pre-cleared for 4 hours at 4° C. with 60 ml blocked CNBr activated Sepharose CL-4B beads, followed by a pre-clearing step for 4 hours at 4° C. with 5 ml of CNBr-activated beads to which human control IgG1 was coupled (1 mg IgG1/ml Cappel) to clear the lysate from proteins that interact aspecifically with IgG. Next, the lysate was passed through a 0.22 μm filter to remove insoluble material. Next, an affinity column of the negative control antibody CR2428 was prepared as described for CR2401 and connected in series to the affinity column of antibody CR2401 and a ÄKTA FPLC 900. The system was equilibrated with TX-100 buffer (1% Triton X-100, 150 mM NaCl, 50 mM Tris pH 7.4, protease inhibitors (Roche)). The lysate was applied to the columns at 1 ml/min and columns were washed with 5 column volumes TX-100 buffer followed by a salt gradient buffer from 150 mM NaCl to 500 mM NaCl, a wash with 5 column volumes TX-100 buffer and an elution with 5 column volumes lysine, pH 11, whereby after 1 column volume of elution buffer the flow through was put on hold for 10 minutes to enhance the release of the immune complexes. Next, the column was washed again with 5 column volumes of TX-100 buffer. The eluted fractions of 0.5 ml were neutralized with 50 µl 0.1 M citric acid and 20 µl of the samples were run on a non-reducing SDS-PAGE Criterion gels and stained with Silver Stain according to standard techniques known to the skilled artisan. The SDS-PAGE profile of the proteins eluting from the CR2401 column showed that a protein of 150 kDa (indicated by the arrow) was specifically released from the column in fraction 8-10 (see, FIG. 5). Fraction 8 contained in addition two protein bands somewhat smaller than 150 kDa (indicated with an asterisk). Then, fraction 8 was 5 times concentrated using YM filters and loaded on a non-reducing SDS-PAGE gel. The 150 kDa band was cut out from the gels with a sharp razor and subjected to mass spectrometry analysis by MALDI-MS or nano-electrospray ionization tandem MS (nanoESI-MS-MS). Using MALDI-MS twelve peptides were identified, i.e., FEVIEFDDGAGSVLR (SEQ ID NO:27), AAGTEGPFQEVDGVATTRYSIGGLSPFSEYAFR (SEQ ID NO:28), TGEQAPSSPPR (SEQ ID NO:29), IQLSWLLPPQER (SEQ ID NO:30), VSWVPPPADSR (SEQ ID NO:31), AHTDVGPGPESSPVLVR (SEQ ID NO:32), IISYTVVFR (SEQ ID NO:33), VAAAMKTSVLLSWEVPDSYK (SEQ ID NO:34), GSSAGGLQHLVSIR (SEQ ID NO:35), WFYIVVVPIDR (SEQ ID NO:36), YANVIAYDHSR (SEQ ID NO:37), and TGCFIVIDAMLERMKHEKTVDIYGHVTCMR (SEQ ID NO:38). One peptide, i.e., NVLELSNVVR (SEQ ID NO:39), was identified by nanoESI-MS-MS. The peptides were identified by blast analysis as being part of the human protein LAR PTP (see, accession number 4506311 in the NIH BLAST database). The amino acid sequence of human LAR PTP is also depicted in SEQ ID NO:40.

Figure 6:
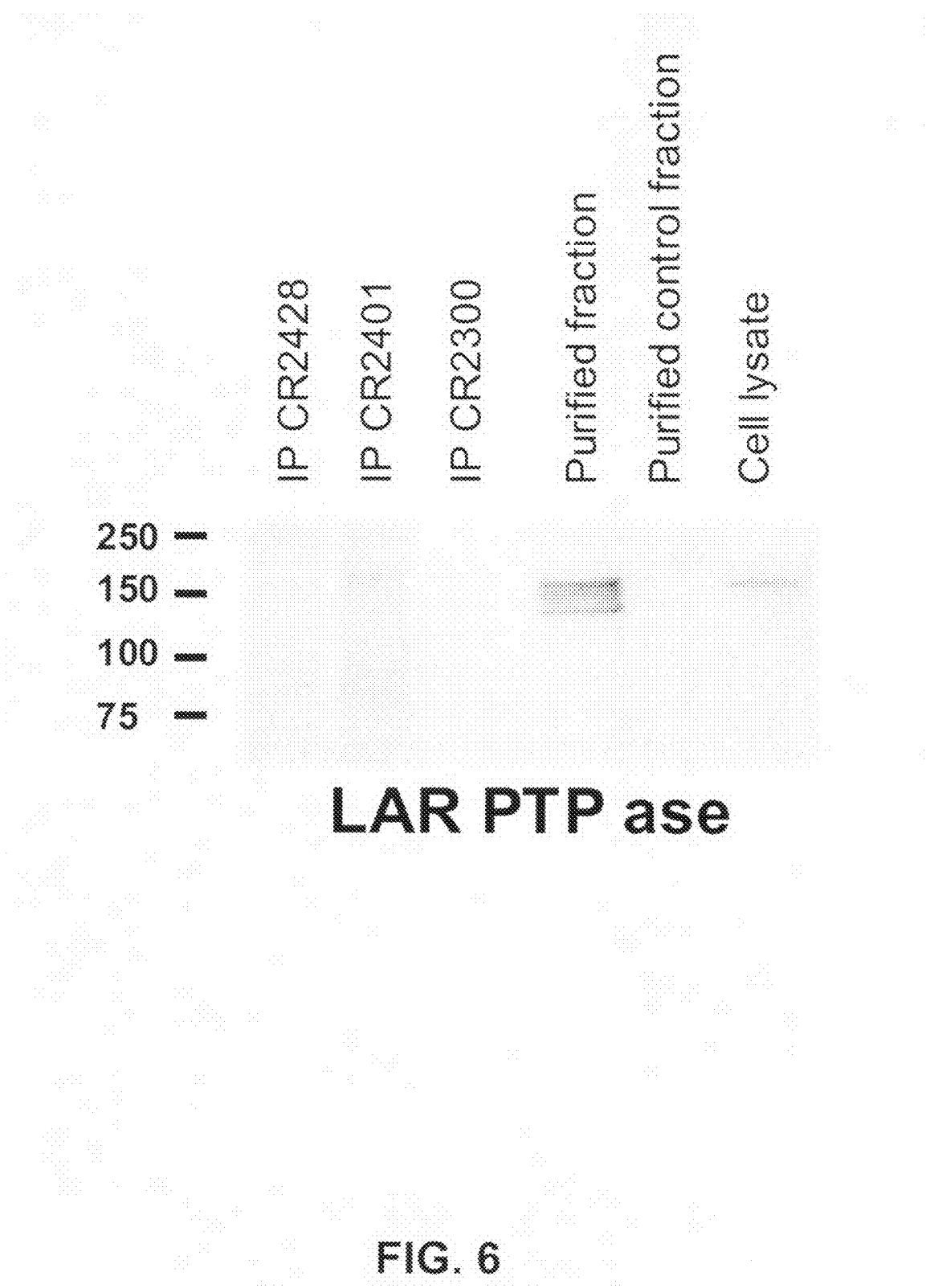
FIG. 6 shows an immunoblot using a murine anti-LAR PTP antibody. On the left side the molecular weight markers are indicated. From left to right are shown, an immunoprecipitate of the negative control antibody CR2428, an immunoprecipitate of the antibody CR2401, an immunoprecipitate of the positive control antibody CR2300, a purified fraction, a purified control fraction and a complete LS174T cell lysate.

To confirm the identification of LAR PTP as the target antigen recognized by CR2401, the purified fraction 8, a negative control fraction, a positive cell lysate and the immunoprecipitation lysates of CR2428, CR2300 and CR2401 were analyzed for the presence of LAR PTP using a LAR PTP-specific murine monoclonal antibody. The samples were subjected to SDS-PAGE under non-reducing conditions to prevent cross-reactivity with immunoglobulin bands that migrate around 55 and 25 kDa. After blotting on PVDF membranes, the membranes were placed in TBST-buffer containing 4% non-fat milk powder and incubated with 1 µg/ml of the murine monoclonal antibody directed against LAR PTP (BD) (in TBST/milk) for 1 hour at room temperature followed by a three-times wash of 5 minutes in TBST. Next, the membranes were incubated with horseradish conjugated rabbit anti-mouse antibody (DAKO) (1 µg/ml in TBST/milk) for one hour at room temperature. Finally, the membranes were washed extensively in TBST followed by a PBS washing step and reactive proteins were revealed by a chemofluorescence detection system (ECL). As demonstrated in FIG. 6, LAR PTP was detected in the CR2401 immunoprecipitate, whereas no reactive band was observed in the negative (CR2428) and positive control (CR2300) immunoprecipitates. Furthermore LAR PTP was present in the cell lysate and eluted fraction, but absent in the control fraction. Two additional bands of a slightly lower molecular weight also reacted with the murine anti-LAR PTP antibody in the eluted fraction. These bands might represent potential LAR PTP degradation products that were also observed on the silver stained gel of the eluted fractions as depicted by the asterisk in FIG. 5 supra.

Figure 7:
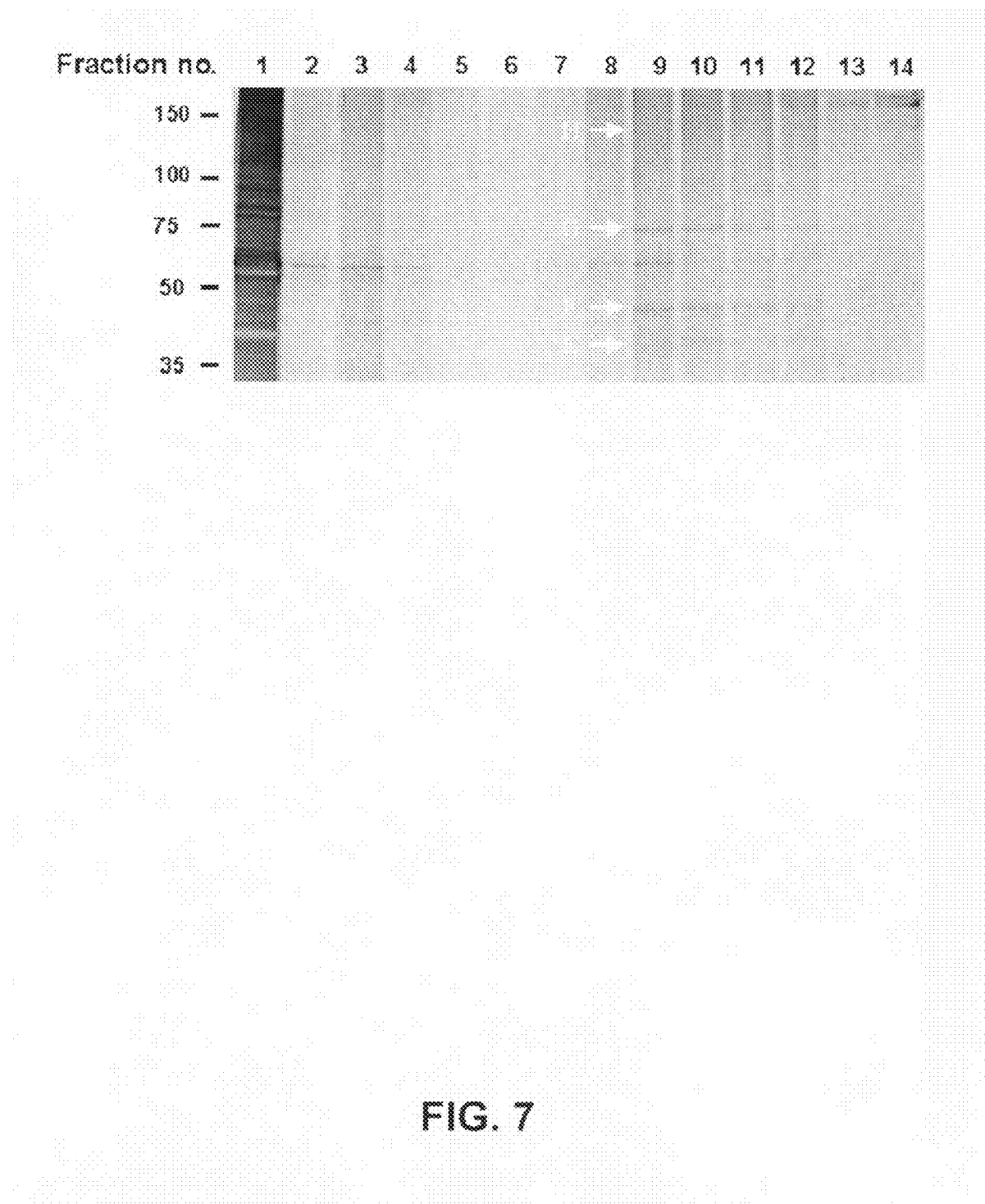
FIG. 7 shows a silver stained SDS-PAGE gel of the proteins eluting from an affinity column of CR2361. The arrows indicate the proteins of interest (30, 40, 75 and 150 kDa; E, F, G and H, respectively) specifically released from the column in fraction 9-12. On the left side the molecular weight markers are indicated.

For the purification of the target antigen of CR2361, an affinity column was prepared as described above for CR2401. A cell lysate of $4*10^9$ NB4 cell was prepared in RIPA buffer, according to the method described in Example 5. The cell lysate was treated essentially as described above and applied to the negative control affinity column that was connected in series to the CR2361 affinity column and an AKTA FPLC 900. The system was equilibrated with RIPA buffer. The lysate was applied to the columns at 1 ml/min and the columns were washed with 5 column volumes of RIPA buffer, followed by a salt gradient from 150 mM NaCl to 500 mM NaCl, a wash with 5 column volumes TX-100 buffer (1% Triton X-100, 150 mM NaCl, 50 mM Tris pH 7.4, protease inhibitors (Roche)) and an elution of 5 column volumes glycine, pH 2.7, whereby after 1 column volume of elution buffer the flow through was put for 10 minutes on hold to enhance the release of immune complexes. Next, the column was washed with 5 column volumes of TX-100 buffer. The eluted fractions of 0.5 ml were neutralized with 20 µl 2 M Tris/HCl, pH 7.4, and 20 µl of the samples were run on a non-reducing SDS-PAGE Criterion gel and stained with silver stain according to standard techniques known to the skilled artisan. The SDS-PAGE profile of the proteins eluting from the CR2361 column shows that proteins with a molecular weight of 30, 40, 75 and 150 kDa (indicated by the arrows and the letters E, F, G and H in FIG. 7) were released from the column. The four bands were cut out from the gels with a sharp razor, de-stained, and digested in the gel using trypsin. The conditions used were according to Pappin et al. Briefly, de-staining was performed using a freshly prepared 1/1 mixture of 30 mM potassium ferricyanide ($K_3Fe(CN)_6$) and 100 mM sodium thiosulfate ($Na_2SO_3$). The gel bands were washed three times with 50 mM $NH_4HCO_3$ in 30% acetonitril and subsequently dried by incubation with pure acetonitrile. The tryptic digest was performed overnight at 37° C. (75 ng trypsin in 4.2 µl 5 mM Tris, pH 8). After digestion, the peptides were eluted with 60% acetonitril and 1% TFA. The samples were desalted using C18-ZipTips (Millipore) according to the manufacturer's instructions. The eluted peptides were mixed 1:1 with a solution of MALDI matrix (2,5-dihydroxybenzoic acid (DHB): 2-hydroxy-5-methoxybenzoic acid 9:1) and analyzed by MALDI-MS (Voyager STR, Applied Biosystems). The resulting peptide masses were used for database search against the NCBInr database using the software ProFound (Genomic solutions).

Several peptides were identified from the 30, 40, and 75 kDa proteins. No peptides were identified from the 150 kDa protein. Peptides identified from the 30 kDa band were MSWLFGINK (SEQ ID NO:41), TLSEETR (SEQ ID NO:42), QTVLESIRTAGTLFGEGFR (SEQ ID NO:43), and LGKPSLVR (SEQ ID NO:44). Peptides identified from the 40 kDa band were WSNFDPTGLER (SEQ ID NO:45), ITVLEALR (SEQ ID NO:46), and CSEVARLTEGMSGR (SEQ ID NO:47). Peptides identified from the 75 kDa band were AARELEHSR (SEQ ID NO:48), QRYEDQLK (SEQ ID NO:49), DIAIATR (SEQ ID NO:50), ATLNAFLYR (SEQ ID NO:51), MYFDKYVLKPATEGK (SEQ ID NO:52), LAQFDYGR (SEQ ID NO:53), and VQDAVQQHQQKMCWLKAEGPGR (SEQ ID NO:54). Peptides identified from the 30 and 40 kDa bands were GLGDRPAPK (SEQ ID NO:55), ATVEREMELR (SEQ ID NO:56), AERENADIIR (SEQ ID NO:57), NATLVAGR (SEQ ID NO:58), and NILMYGPPGTGK (SEQ ID NO:59). Finally, the peptides identified from the 30, 40 and 75 kDa band were GEGAGP- PPPLPPAQPGAEGGGDR (SEQ ID NO:60) and QQQLL-NEENLR (SEQ ID NO:61). The peptides were identified by blast analysis as being part of a human protein having the amino acid sequence SEQ ID NO:6 (see, accession number AAH63607 in the NIH BLAST database). This protein has been given the name ATAD3A, but no function has been assigned to the protein. The nucleotide sequence of ATAD3A has the nucleotide sequence of SEQ ID NO:5.

Figure 8:
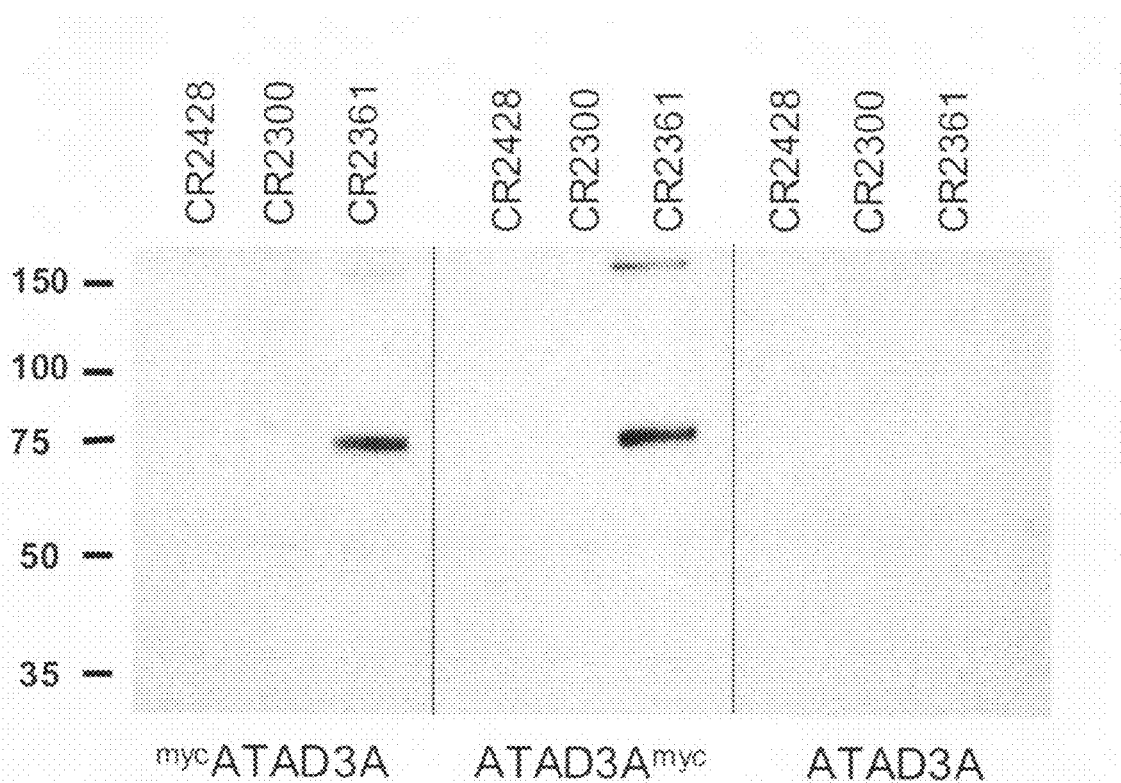
FIG. 8 shows immunoblots of HEK93T cells transfected with ATAD3A, mycATAD3A and ATAD3Amyc constructs (right, left and middle part of blot, respectively). Cells were lysed and cell lysates obtained were biotinylated and immunoprecipitated with the negative control antibody CR2428, the positive control antibody CR2300 and antibody CR2361. Immunoblots were developed with anti-myc. On the left side the molecular weight markers are shown.
Figure 9:
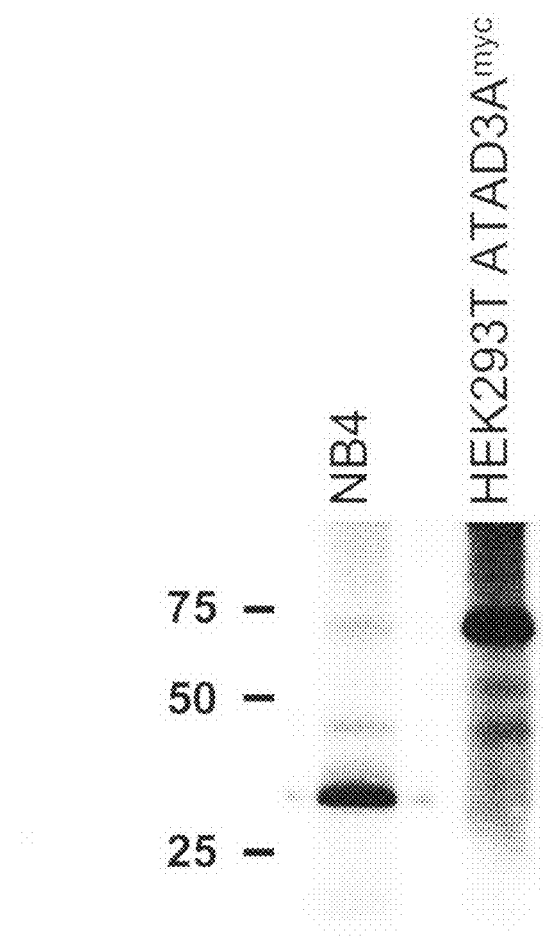
FIG. 9 shows an immunoblot of a cell surface biotinylated NB4 cell lysate immunoprecipitated with CR2361 (left lane) and a complete cell lysate of HEK293T cells transfected with ATAD3Amyc (right lane). On the left side of the blot molecular weight markers are indicated.

To confirm the identification of ATAD3A as the target antigen recognized by CR24361, mRNA was extracted from $2*10^7$ NB4 cells using the nucleotrap mRNA mini purification kit (Becton Dickinson) according to protocols provided by the manufacturer. Then, RT-PCR was performed on the mRNA isolated. For the PCR, the following primers were designed: forward primer 5'-GTGCGAGCATGTCGTGGC-3' (SEQ ID NO:62) and reverse primer 5'-GGAGATCCA-CAGCTCACGG-3' (SEQ ID NO:63). PCR was performed with Pfu (Promega) in the presence of 5% DMSO and resulted in a 1800 bp product. The resulting fragment was cloned in the pCR4TOPO vector (Invitrogen) and transformed into DH5α cells. The resulting clone was verified by sequence analysis and aligned with the sequence present in the database. The protein construct was subsequently digested with EcoRI and cloned in the corresponding sites of pcDNA3.1 zeo, to create construct ATAD3ApcDNA3.1zeo. To simplify the detection of the protein in the subsequent transfection experiments, the protein was fused with a myc tag at the 5' prime or 3' prime end by means of PCR (using the construct as a template). For the 5' myc construct the following primers were designed: forward primer 5'-CGGGATC-CAGCATGGAACAAAAACTTATTTCTGAA-GAAGATCTGTCGTGGCTCTTCGCA TTAACAAG-3' (SEQ ID NO:64) and reversed primer 5'-CGGAATTCGACT-CAGGATGGGGAAGGC-3' (SEQ ID NO:65). For the 3' myc construct the primers were constructed in such a way that the protein became in frame with the myc tag in pcDNA3mycA. In that case the forward primer was 5'-CGG-GATCCTGCGAGCATGTCGTGGC-3' (SEQ ID NO:66) and the reverse primer was 5'-GCTCTAGAGGATGGG-GAAGGCTCG-3' (SEQ ID NO:67). PCR was performed using Pfu polymerase and the resulting fragment of the 5' myc tag was cloned BamHI/EcoRI in pcDNA3.1 zeo vector (Invitrogen) resulting in the mycATAD3A construct, whereas the resulting fragment for the 3' myc tag was cloned BamHI/XbaI in pcDNA3.1/hismycA (Invitrogen) resulting in the ATAD3Amyc construct. The constructs were verified by sequencing. All cloning procedures were performed according to standard molecular techniques known to a person skilled in the art. $2*10^7$ HEK293T cells were transfected using the Fugene (Roche) reagent according to protocols provided by the manufacturer with the expression constructs described supra, i.e., ATAD3A, mycATAD3A, ATAD3Amyc and a positive control construct expressing the cell surface receptor CD38. 72 hours after transfection, cells were harvested and stained for FACS analysis with the phage antibody SC02-361 as described in Example 3 supra. The stained cells were analyzed by flow cytometry, but SC02-361 did not stain any transfectants indicating that the protein was not expressed on the surface of the cell. However, Western blot analysis on cell lysates of the transfected cells using an anti-myc antibody according to procedures known to a skilled person in the art revealed that the protein was expressed, probably inside the cell. Next, HEK93T cells transfected with ATAD3A, mycATAD3A and ATAD3Amyc constructs were lysed in 1% Triton X-100 buffer followed by biotinylation of the cell lysate and immunoprecipitation with CR2361 and control antibodies CR2300 and CR2428 as described supra. Immunoblots developed with anti-myc demonstrated that protein that was 3' or 5' myc-tagged and present in the cytoplasmic fraction was immunoprecipitated by CR2361 and not by the control antibodies (see, FIG. 8). Immunoprecipitations with biotinylated complete cell lysates of NB4 cells and HEK293T transfected cells revealed that the molecular weight of the cloned protein corresponded with a band present at 75 kDa (see, FIG. 9).

TABLE 1

Nucleotide and amino acid sequence of the scFvs and VH and VL gene identity.

| Name scFv | SEQ ID NO of nucleotide sequence | SEQ ID NO of amino acid sequence | CDR3 | VH-germline | VL-germline |
|---|---|---|---|---|---|
| SC02-401 | SEQ ID NO: 11 | SEQ ID NO: 12 | DDTPTSDYGFDS (SEQ ID NO: 1) | 3-20 (DP-32) | Vk I (O12/O2-DPK9) |
| SC02-361 | SEQ ID NO: 13 | SEQ ID NO: 14 | WAPSHSFDY (SEQ ID NO: 2) | 3-43 (DP-33) | Vk I (O12/O2-DPK9) |

TABLE 2

Flow cytometry analysis of binding of SC02-401 to various AML samples.

| FAB | Cases positive (%) | CD33 |
|---|---|---|
| M0 | 100 (1#/1*) | 100 (1#/1*) |
| M1 | 25 (1/4) | 100 (4/4) |
| M1/2 | 100 (1/1) | 100 (1/1) |
| M2 | 0 (0/4) | 100 (4/4) |
| M3 | 100 (1/1) | 100 (1/1) |
| M4 | 20 (1/5) | 100 (5/5) |
| M5 | 50 (2/4) | 75 (3/4) |
| M5a | 33 (1/3) | 100 (3/3) |
| M5b | 0 (0/1) | 100 (1/1) |
| unclassified | 0 (0/4) | 75 (3/4) |
| all | 8/28 | 26/28 |
| Percentage (%) | 29 | 93 | number of positive cases; a sample was considered positive if more than 20% of the blast population stained with SC02-401 or anti-CD33 antibody.
*number of cases tested.

TABLE 3

Flow cytometry analysis of binding of SC02-361 to various AML samples.

| FAB | % positive cases | CD33 |
|---|---|---|
| M0 | 100 (1#/1*) | 100 (1#/1*) |
| M1 | 67 (2/3) | 100 (3/3) |
| M1/2 | 100 (1/1) | 100 (1/1) |
| M2 | 75 (3/4) | 100 (4/4) |
| M3 | 100 (1/1) | 100 (1/1) |
| M4 | 60 (3/5) | 100 (5/5) |
| M5 | 75 (3/4) | 75 (3/4) |
| M5a | 66 (2/3) | 100 (3/3) |
| M5b | 100 (1/1) | 100 (1/1) |
| unclassified | 100 (3/3) | 67 (2/3) |
| all | 20/26 | 24/26 |
| Percentage (%) | 77 | 92 | number of positive cases; a sample was considered positive if more than 20% of the blast population stained with the sc02-361 antibody or anti-CD33 antibody.
*number of cases tested.

TABLE 4

Analysis of tumor cell lines of hematopoetic and non-hematopoetic origin for reactivity with SC02-401 and SC02-361.

| Cell line | Origin | SC02-401 reactivity | SC02-361 reactivity |
|---|---|---|---|
| HL-60 | Acute Myeloid Leukemia | + | +/− |
| NB4 | Acute Promyelocytic Leukemia | + | + |
| U937 | Histiocytic Lymphoma | +/− | +/− |
| K562 | Erythroid Leukemia | + | − |
| 293T | Embryonal Kidney | + | − |
| LS174T | Colon Adenocarcinoma | + | +/− |
| HEp-2 | Cervix Epithelial cells | + | +/− |

Reactivity <5% = −;
reactivity 5-25% = +/−;
reactivity 25-75% = +;
reactivity >75% = ++

TABLE 5

Expression of antigens recognized by SC02-401 and SC02-361 on subsets of peripheral blood as analyzed by FACS.

| | SC02-401 reactivity | SC02-361 reactivity |
|---|---|---|
| Monocytes | − | S[1]+ |
| granulocytes | − | − |
| B cells | − | − |
| T cells | − | − |
| Dendritic cells | − | S[2]+ |
| Natural killer cells | − | − |
| erythrocytes | − | − |
| Platelets | − | − |

S[1]+: 50% of the cells positive;
S[2]+: 40% of the cells positive

REFERENCES

Boel E., S. Verlaan, M. J. Poppelier, N. A. Westerdaal, J. A. Van Strijp, and T. Logtenberg (2000). Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

De Kruif J., L. Terstappen, E. Boel, and T. Logtenberg (1995a). Rapid selection of cell subpopulation-specific human monoclonal antibodies from a synthetic phage antibody library. *Proc. Natl. Acad. Sci. USA* 92:3938.

De Kruif J., E. Boel and T. Logtenberg (1995b). Selection and application of human single chain Fv antibody fragments from a semi-synthetic phage antibody display library with designed CDR3 regions. *J. Mol. Biol.* 248:97.

Huls G., I. J. Heijnen, E. Cuomo, J. van der Linden, E. Boel, J. van de Winkel and T. Logtenberg (1999). Antitumor immune effector mechanisms recruited by phage display-derived fully human IgG1 and IgA1 monoclonal antibodies. *Cancer Res.* 59:5778-5784.

Pappin D. J. C., P. Hojrup and A. Bleasby (1993). Rapid identification of proteins by peptide-mass fingerprinting. *Curr. Biol.* 3:327-332.

Streuli M., N. X. Krueger, L. R. Hall, S. F. Schlossman, and H. Saito (1988). A new member of the immunoglobulin superfamily that has a cytoplasmic region homologous to the leukocyte common antigen. *J. Exp. Med.* 168:1523-1530.

Streuli M., N. X. Krueger, P. D. Ariniello, M. Tang, J. M. Munro, W. A. Blattler, D. A. Adler, C. M. Disteche, and H. Saito (1992). Expression of the receptor-linked protein tyrosine phosphatase LAR: proteolytic cleavage and shedding of the CAM-like extracellular region. *EMBO J.* 11:897-907.

What is claimed is:

1. An isolated binding molecule which binds to an antigen present on acute myeloid leukemia (AML) cells, wherein the binding molecule comprises: a heavy chain variable region comprising SEQ ID NO:3 and a light chain variable region comprising SEQ ID NO: 7.

2. The binding molecule of claim 1, wherein the binding molecule is human.

3. The binding molecule of claim 2, wherein the binding molecule is able to specifically bind to leukocyte antigen related receptor protein tyrosine phosphatase.

4. The binding molecule of claim 3, wherein the binding molecule comprises at least a heavy chain CDR3 region comprising SEQ ID NO:1.

5. The binding molecule of claim 3, wherein the binding molecule has specific immunoreactivity with acute myeloid leukemia (AML) subtypes M0, M1/2 and M3.

6. The binding molecule of claim 1, wherein the antigen is leukocyte antigen related receptor protein tyrosine phosphatase.

7. An immunoconjugate comprising the binding molecule of claim 1, and a tag.

8. A pharmaceutical composition comprising:
the binding molecule of claim 1, and
a pharmaceutically acceptable carrier.

9. A composition for detecting acute myeloid leukemia (AML), the composition comprising: the binding molecule of claim 3.

10. A pharmaceutical composition comprising:
the binding molecule of claim 3, and
a pharmaceutically acceptable carrier.

11. A method for producing the binding molecule of claim 1, the method comprising: expressing in an isolated host cell a vector comprising a nucleic acid molecule encoding said binding molecule.

12. The method according to claim 11, wherein the host cell is a human cell.

* * * * *